US007749694B2

(12) United States Patent
Ghosh et al.

(10) Patent No.: US 7,749,694 B2
(45) Date of Patent: Jul. 6, 2010

(54) C-TYPE LECTIN FOLD AS A SCAFFOLD FOR MASSIVE SEQUENCE VARIATION

(75) Inventors: Partho Ghosh, San Diego, CA (US); Stephen McMahon, Renfrew (GB); Jason Miller, Carlsbad, CA (US); Jeffrey Lawton, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 501 days.

(21) Appl. No.: 11/027,323

(22) Filed: Dec. 31, 2004

(65) Prior Publication Data

US 2007/0275367 A1 Nov. 29, 2007

(51) Int. Cl.
*C12Q 1/00* (2006.01)
*C12Q 1/04* (2006.01)
*A61K 38/16* (2006.01)

(52) U.S. Cl. ............................ 435/4; 435/34; 530/350; 530/395

(58) Field of Classification Search ....................... None
See application file for complete search history.

(56) References Cited

U.S. PATENT DOCUMENTS

| | | | |
|---|---|---|---|
| 5,223,409 | A | 6/1993 | Ladner et al. |
| 5,571,698 | A | 11/1996 | Ladner et al. |
| 6,818,418 | B1 | 11/2004 | Lipovsek et al. |

FOREIGN PATENT DOCUMENTS

| | | |
|---|---|---|
| WO | WO99/16873 | 4/1999 |
| WO | WO00/60070 | 10/2000 |

OTHER PUBLICATIONS

Liu et al., Genomic and genetic Analysis of *Bordetella* Bacteriophages Encoding Reverse Transcriptase-Mediated Tropism-Switching Cassettes, J. Bacteriology, 2004, p. 1503-1517.*
NCBI Sequence Viewer, pp. 1-2.*
Taylor, Maureen E., et al. "Structure-Function Analysis of C-Type Animal Lectins", *Methods in Enzymology* (2003) 363:3-16.
Drickamer, Kurt, "C-type lectin-like domains", *Current Opinion in Structural Biology* (1999) 9:585-590.
Drickamer, Kurt, "Two Distinct Classes of Carbohydrate-recognition Domains in Animal Lectins", *The Journal of Biological Chemistry*, (1988) 263(20):9557-9560.
Hirabayashi, Jun, et al. "Effect of Amino Acid Substitution by Site-directed Mutagenesis on the Carbohydrate Recognition and Stability of Human 14-kDa β-Galactoside-binding Lectin", *The Journal of Biological Chemistry* (1991) 266(35):23648-23653.
Kogelberg, Heide, et al. "New structural insights into lectin-type proteins of the immune system", *Current Opinion in Structural Biology* (2001), 11:635-643.
Weis, William I., et al. "Structure of the Calcium-Dependent Lectin Domain from a Rat Mannose-Binding Protein Determined by MAD Phasing", *Science* (1991) 254:1608-1615.
Sharon, Nathan, et al. "History of lectins: from hemagglutinins to biological recognition molecules", *Glycobiology* (2004) 14(11):53R-62R.
Luo, Yu, et al. "Crystal structure of enteropathogenic *Escherichia coli* Intimin-receptor complex", *Nature*, (2000) 405:1073-1077.
Bowen, Benjamin R., et al. "Characterization of a Human Homologue of the Murine Peripheral Lymph Node Homing Receptor", *The Journal of Cell Biology* (1989) 109:421-427.
Akerley, B.J., et al. "Ectopic expression of the flagellar regulon alters development of the *Bordetella*-host interaction", *Cell* (1995) 80:611-620.
Batchelor, M., et al. "Structural basis for recognition of the translocated intimin receptor (Tir) by intimin from enteropathogenic *Escherichia coli", EMBO J.* (2000) 19:2452-2464.
Beste, G., et al. "Small antibody-like proteins with prescribed ligand specificities derived from the lipocalin fold", *Proc. Natl. Acad. Sci USA* (1999) 96:1898-1903.
Cotter, P.A., et al. "A mutation in the *Bordetella bronchiseptica* bvgS gene results in reduced virulence and increased resistance to starvation, and identifies a new class of Bvg-regulated antigens", *Mol. Microbiol.* (1997) 24:671-685.
Davis, M.M., et al. "T-cell antigen receptor genes and T-cell recognition", *Nature* (1988) 334:395-402.
Doulatov, S., et al. "Tropism switching in *Bordetella* bacteriophage defines a family of diversity-generating retroelements", *Nature* (2004) 431:476-481.
Emsley, P., et al. "Crystallographic characterization of pertactin, a membrane-associated protein from *Bordetella pertussis" J. Mol. Biol* (1994) 235:772-773.
Emsley, P., et al. "Structure of *Bordetella pertussis* virulence factor P.69 pertactin", *Nature* (1996) 381:90-92.
Hester, G., et al. "Structure of mannose-specific snowdrop (*Galanthus nivalis*) lectin is representative of a new plant lectin family", *Nat. Struct. Biol.* (1995) 2:472-479.
Holm, L., et al. "Protein structure comparison by alignment of distance matrices", *J. Mol. Biol.* (1993) 233:123-138.
Lasky, *Annu. Rev. Biochem.* (1995) 64:113-139.
Liu, M., et al. "Reverse transcriptase-mediated tropism switching in *Bordetella* bacteriophage", *Science* (2002) 295:2091-2094.
Mooi, F.R., et al. "Polymorphism in the *Bordetella pertussis* virulence factors P.69/pertactin and *pertussis* toxin in The Netherlands: temporal trends and evidence for vaccine-driven evolution", *Infect. Immun.* (1998) 66:670-675.
Tormo, J., et al. "Crystal structure of a lectin-like natural killer cell receptor bound to its MHC class I ligand", *Nature* (1999) 402:623-631.
Uhl, M.A., et al. "Integration of multiple domains in a two-component sensor protein: the *Bordetella pertussis* BvgAS phosphorelay", *EMBO J.* (1996) 15:1028-1036.
Weis, W. I., et al. "Structure of a C-type mannose-binding protein complexed with an oligosaccharide", *Nature* (1992) 360:127-134.

* cited by examiner

*Primary Examiner*—Jon P Weber
*Assistant Examiner*—Kagnew H Gebreyesus
(74) *Attorney, Agent, or Firm*—DLA Piper LLP (US)

(57) ABSTRACT

This invention provides a class of binding proteins with a range of binding specificities and affinities based upon variation at select amino acid positions within a scaffold. The variable positions may be readily modified to produce a library of binding proteins with different binding specificities and affinities. The library may be screened to identify one or more as binding a ligand of interest. Compositions comprising the binding proteins, as well as methods of using the binding proteins are also provided.

9 Claims, 11 Drawing Sheets
(11 of 11 Drawing Sheet(s) Filed in Color)

C-TYPE LECTIN FOLD AS A SCAFFOLD FOR MASSIVE SEQUENCE VARIATION

STATEMENT AS TO RIGHTS TO INVENTIONS MADE UNDER FEDERALLY SPONSORED RESEARCH AND DEVELOPMENT

The present invention was supported in part with funding provided by Grant Nos. T32 GM008326, F31 AI061840, and F32AI49695 from the National Institutes of Health. The federal government may have certain rights to this invention.

FIELD OF THE INVENTION

This invention relates to a class of binding proteins with a range of binding specificities and affinities based upon variation at select amino acid positions within a scaffold. The variable positions may be readily modified to produce a variety of binding proteins with different binding specificities and affinities. This range of proteins may be screened to identify one or more as binding a target molecule of interest. Compositions comprising the binding proteins, as well as methods of using the binding proteins are also provided.

BACKGROUND OF THE INVENTION

The amino acid sequence of a protein determines its secondary, tertiary, and quaternary structure to result in the protein's final three-dimensional (3D) shape. The shape and functional groups (side chains) of the amino acids therein define the protein's function. In the case of a binding protein, the portion of the protein responsible for the binding activity (binding domain) must either be exposed, or be capable of being exposed, on an accessible surface of the protein exposed to the exterior solvent to provide for possible interaction with a binding target. Thus to vary the binding activity, the amino acid residues of the binding domain must be varied.

With an immunoglobulin as an example of a familiar binding protein with specificity and affinity, the "variable region" or binding domain includes six loops clustered in space. The loops provide the 6 complementarity determining regions (CDRS) and are contained in two polypeptides, a heavy chain and a light chain, each carrying 3 CDRs (H1, H2, and H3 of the heavy chain and L1, L2, and L3 of the light chain). The amino acid residues of the variable regions orient the CDRs toward the exterior solvent environment to permit their interaction with an antigen. High sequence variability of the amino acid residues of the CDRs allows immunoglobulins as a class to bind a large variety of antigens. The CDRs and non-CDR portion of the variable region form an immunoglobulin fold to determine the structure of the loops and thereby maintain the overall structure of the immunoglobulin variable region, with proper orientation of the CDRs.

But variability in the sequence of a protein, like an immunoglobulin, is often limited by the effects of variability on protein folding and the resulting final 3D shape. Amino acid residues with side chains that are not exposed to the exterior solvent are often limited in variability because as part of the protein's interior they must "fit" within the interior space as dictated by other amino acid residues. The protein can tolerate greater variability in residues with side chains oriented toward, and exposed to, the exterior solvent, given that they do not have to "fit" into an interior space constrained by other residues.

To diversify the binding functionality of a binding protein and thus promote recognition of members of a diverse population of target molecules, amino acid variability is necessary.

Interactions between a binding protein and its target molecule (the ligand) are usually non-covalent and yet often very tight (high affinity or avidity) and specific. The intermolecular interactions are defined by the amino acid residues of the protein's binding domain which form a surface that fits "hand-in-glove" like onto the surface of the ligand being bound. The two contacting surfaces must have complementarity via hydrogen bonding (at times mediated by a water molecule), charge interactions, alignment of attracting dipoles, hydrophobic to hydrophobic (van der Waals) interactions, and/or protrusions fitting with depressions.

In the example of an immunoglobulin, the binding domain is presented within the context of the framework made up by the rest of the immunoglobulin molecule. The framework, generally referred to as the immunoglobulin fold, forms the scaffold of the protein structure and functions to correctly present the binding domain. The framework restrains the 3D shape of the protein so that the amino acid residues of the binding domain are positioned in a manner to create the accessible specific binding site.

The usefulness of immunoglobulins as manipulable binding proteins is limited, however, by the nature of the immunoglobulin framework, which requires two polypeptides to form the complete ligand- or antigen-binding site. This results in a number of disadvantages: the need to manipulate rather large polypeptides, the need for complicated molecular cloning to diversify a binding site; and the complication of modifying six different CDRs. The consequences of these disadvantages include constraints on using phage display (see for example U.S. Pat. Nos. 5,223,409 and 5,571,698) to diversify immunoglobulins for the purpose of creating new binding or other functional activities.

A number of attempts have been made to overcome the limitations of immunoglobulins. These include the use of a CTL4-like sandwich architecture as a framework for presenting randomized peptide sequences (see WO 00/60070); the use of fibronectin type III domains (see U.S. Pat. No. 6,818,418); the use of an "anticalin" (see WO 99/16873 and Beste et al. *Proc. Natl. Acad. Sci., USA* 96:1898-1903 (1999)); and even the use of single chain antibodies, optionally with a CH3 domain of an immunoglobulin to permit spontaneous dimerization.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

The present invention is related to the discovery of a diversity-generating retroelement (DGR) belonging to a *Bordetella* bacteriophage. The DGR has recently been shown to be capable of producing massive, targeted amino acid sequence variation in the phage's receptor-binding protein, the major tropism determinant (Mtd). See Liu, M. et al. "Reverse transcriptase-mediated tropism switching in *Bordetella* bacteriophage." *Science* 295, 2091-4 (2002); Liu, M. et al. "Genomic and genetic analysis of *Bordetella* bacteriophages encoding reverse transcriptase-mediated tropism-switching cassettes." *J Bacteriol* 186, 1503-17 (2004); and Doulatov, S. et al. "Tropism switching in *Bordetella* bacteriophage defines a family of diversity-generating retroelements." *Nature* 431, 476-81 (2004). This genetically programmed diversity, with ~$10^{13}$ different Mtd sequences possible, is rivaled in scale only by antibodies (immunoglobulins) and T cell receptors in the immune system (see Davis, M. M. & Bjorkman, P. J. "T-cell antigen receptor genes and T-cell recognition." *Nature* 334, 395-402 (1988)).

As noted above, whereas the immune system requires variability in numerous gene segments to achieve antigen-binding diversity, the *Bordetella* phage DGR utilizes a single copy of mtd followed by a nearly identical (90%), 134-bp direct repeat of the 3' end of mtd (see FIG. 1 herein). Genetic information in this direct repeat, called the template repeat (TR) due to its invariance, is converted into a cDNA altered by random insertion of A, G, C, or T specifically at sites occupied by adenines in TR through the action of a DGR-encoded reverse transcriptase. The mutagenized sequence is then substituted into the variable region (VR) of mtd by a process known as mutagenic homing, thereby producing an Mtd variant. Due to the adenine dependency of the mutagenic process mediated by the DGR reverse transcriptase, 12 amino acid residues in VR, encoded by codons corresponding to nucleotide triplets in TR with adenine residues at non-wobble positions, are subject to variation at high frequency. The effect of the resulting amino acid variation in VR is to alter the binding specificity of Mtd and consequently host tropism for the phage. These alterations are crucial to the phage's survival because its host, *Bordetella*, undergoes phase variation under different environmental conditions, and the expression patterns of bacterial cell surface receptors, such as pertactin change with the phase. For example, Bvg-plus tropic phage-1 (BPP-1) infects only $Bvg^+$ *Bordetella*, the pathogenic phase, since the Mtd-P1 variant expressed by this phage uses as its receptor the $Bvg^+$-specific outer membrane protein, pertactin. When *Bordetella* encounters an ex vivo environment, it ceases expressing pertactin, becoming $Bvg^-$ as it concomitantly becomes resistant to infection by BPP-1 (see Uhl, M. A. & Miller, J. F. "Integration of multiple domains in a two-component sensor protein: the *Bordetella pertussis* BvgAS phosphorelay." *EMBO J* 15, 1028-36 (1996)).

However, the phage counters by producing Mtd variants, such as Mtd-M1, that use unknown receptors expressed exclusively by $Bvg^-$ *Bordetella*, thereby creating Bvg-minus tropic phage (BMP). Alternatively, Mtd variants, such as Mtd-I1, are produced that infect through unknown receptors expressed by both phases of *Bordetella*, thereby creating Bvg-indiscriminant phage (BIP). Mtd variants, such as Mtd-3c, that confer infectivity towards $Bvg^+$ *Bordetella* but use instead of pertactin, an unknown receptor, have also been found. The molecular protein structure with which Mtd creates diverse receptor-binding sites and tolerates massive sequence variation was not known prior to the present invention.

Mtd is found on the tails of *Bordetella* bacteriophage, which number 6 per phage particle. Based upon the discovery described herein, there appear to be 3 Mtd monomers per phage tail, and thereby 18 Mtd monomers per phage particle.

The invention is based in part on the discovery of the unexpected structures of multiple Mtd variants. The basic structure is a pyramid-shaped homotrimer with variable amino acid residues organized along the pyramid base by a C-type lectin (CTL)-fold that creates a discrete receptor-binding site in each of the three monomers. The present invention thus provides the use of the CTL-fold, or portion thereof, as a scaffold to orient the side chains of variable amino acid residues toward the external solvent environment. The side chains of the variable amino acid residues define, in whole or in part, the three dimensional structure or shape of all or part of the binding site, which is attached to the scaffold through the alpha carbons of each variable amino acid residue.

The present invention also provides for the use of CTL-folds as a scaffold for massive sequence variation of the variable amino acid residues, and thus the side chains thereof, in the manner exemplified by *Bordetella* bacteriophage. The availability of $\sim 10^{13}$ possible combinations of variable amino acid residue side chains in the binding site provides a highly diverse population of binding proteins with different specificities. The extraordinary diversity available in this localized portion of the binding site provided by the scaffold provides differing shapes and chemical reactivities suitable for binding to and operating on a wide range of target molecules. This level of diversity provided to the binding site of a CTL-fold by the present invention is paralleled only by the antigen binding region of immunoglobulins and T cell receptors in the immune system. But unlike those examples, the binding proteins of the invention may be produced by modification of a single polypeptide chain to result in a highly diverse population of binding proteins. The single chain can be modified via recombinant methods, such as by recombinant use of the elements of the DGR of *Bordetella* bacteriophage.

The scaffold, or backbone conformation, present in the CTL-fold has been observed to provide a stable structure for the presentation of a binding site. As noted by Kogelberg et al. (Curr. Opin. Structural Biol., 11:635-643, 2001), the CTL-fold has closely spaced N and C termini which are opposite the binding site of the fold. Thus the invention provides for the use of the CTL-fold to present a binding site with variable residues that may be varied without compromising the maintenance of the structural integrity of the CTL-fold. In the case of Mtd, the scaffold structure includes stabilization of loops in the binding site by two inserts and trimeric intertwining as well as other structures contributing to the CTL fold. In the case of other CTL-folds, the scaffold is similarly stabilized by the structures present in the scaffold, such as, but not limited to, the presence of disulfide bridges that contribute to the integrity of the CTL fold. The CTL-fold, therefore, provides a stable, highly tolerant scaffold for combinatorial display of the side chains of variable amino acid residues used to form all or part of a binding site.

The availability of a scaffold to present diverse binding sites permits the generation of binding proteins with different specificities and affinities for binding a wide number of different target molecules, particularly biomolecules. The binding proteins may be used to bind, and thus detect, identify, localize or modify, such target molecules.

The invention thus provides, in one aspect, for a protein scaffold comprising a variable binding site comprising the amino acid sequence (SEQ ID NO:1)

$-Xaa_1-Trp-Xaa_2-Xaa_3-Xaa_4-Ser-Xaa_5-Ser-Gly-Ser-Arg-$ $Ala-Ala-Xaa_6-Trp-Xaa_7-Xaa_8-Gly-Pro-Ser-Xaa_9-Ser-$ $Xaa_{10}-Ala-Xaa_{11}-Xaa_{12}-$ wherein each of $Xaa_1$ to $Xaa_{12}$ is independently any amino acid residue, the side chains of which form a binding site, in whole or in part.

The scaffold serves as a framework to present variable amino acid residues, the side chains of which form the binding site of the protein. Preferably, the scaffold is derived from, and forms all or part of, a CTL-fold which displays or exposes the binding site to the external solvent environment. Thus the invention includes the above sequence (wherein SEQ ID NO:1 constitutes all or part of the binding side of the scaffold) in a non-Mtd, CTL-fold as the scaffold. The scaffold may optionally be conjugated to another polypeptide or other molecule through residues distant from the binding site.

In another aspect, the invention also provides a binding protein comprising a scaffold as described above. The binding specificity of the protein is determined by the variable binding site, and the protein comprises a scaffold comprising the amino acid sequence (SEQ ID NO:1)
-$Xaa_1$-Trp-$Xaa_2$-$Xaa_3$-$Xaa_4$-Ser-$Xaa_5$-Ser-Gly-Ser-Arg- Ala-Ala-$Xaa_6$-Trp-$Xaa_7$-$Xaa_8$-Gly-Pro-Ser-$Xaa_9$-Ser- $Xaa_{10}$-Ala-$Xaa_{11}$-$Xaa_{12}$- wherein each of $Xaa_1$ to $Xaa_{12}$ is independently any amino acid residue, the side chains of which form a binding site, in whole or in part, that determines the binding specificity of the protein; and at each of the $Xaa_1$ and $Xaa_{12}$ ends of the scaffold are amino acid sequences that form a superscaffold which displays said binding site in a solvent exposed portion of the protein, or one of the $Xaa_1$ and $Xaa_{12}$ ends of the scaffold is —H (a covalently bonded hydrogen atom) and the other end is an amino acid sequence that forms a superscaffold which displays said binding site in a solvent exposed portion of the protein.

The side chains of the variable (Xaa) residues may form the whole of the binding site where no other side chains of the protein contribute to binding interactions with a target molecule bound by the protein. Alternatively, other side chains of the protein, such as those of other amino acid residues in the scaffold or superscaffold, may contribute to the binding interactions with a target molecule. In this case, the side chains of the variable residues only compose part of the binding site of the protein. Non-limiting examples of a target molecule include a viral antigen, a bacterial antigen, a fungal antigen, an enzyme, an enzyme inhibitor, a cell surface molecule of any composition, a reporter molecule, a serum protein, and a receptor. In the case of a viral antigen as a target molecule, it may be, but is not limited to, a polypeptide required for replication. Thus the binding sites of the invention, like immunoglobulin binding sites, recognize proteins (including native, denatured, and proteolytic forms thereof as well as conformational determinants thereof); nucleic acids; polysaccharides (alone or as modifications on another molecule, such as a protein); lipids; and small chemical molecules (like haptens in the case of an antibody).

Optionally, the scaffold is extended at the $Xaa_1$ end by all or part of the sequence -Ala-Ala-Leu-Phe-Gly-Gly- (SEQ ID NO:2), wherein the extension may be by 1, 2, 3, 4, 5, or all 6 of the consecutive amino acid residues of SEQ ID NO:2 linked to $Xaa_1$ via the carboxyl end of the last Gly residue in SEQ ID NO:2. Alternatively, the scaffold is extended at the $Xaa_{12}$ end by all or part of the sequence -Gly-Ala-Arg-Gly-Val-Cys-Asp-His-Leu-Ile-Leu-Glu (SEQ ID NO:3), wherein the extension may be by 1, 2, 3, 4, 5, 6, 7, 8, 9, 10, 11, or all 12 of the consecutive amino acid residues linked to $Xaa_{12}$ via the amino end of the first Gly residue in SEQ ID NO:3. The scaffold may also be extended at both ends by any combination of the above extensions at $Xaa_1$ and $Xaa_{12}$ followed by further optional extensions. Where all 12 amino acids of SEQ ID NO:3 are present in a scaffold, preferred embodiments of the invention have no further extension at the C terminus by additional amino acid residues.

The superscaffold is composed of additional amino acids attached to a scaffold of the invention without adverse effect on the binding site contained therein. A binding protein of the invention is thus preferably composed of a binding site within a scaffold which is attached to a superscaffold. Preferably, the superscaffold is composed of amino acids associated with the scaffold in naturally occurring sources of the scaffold, such as in naturally occurring polypeptides with a CTL-fold. Alternatively, the scaffold may be grafted onto a heterologous superscaffold, such as the superscaffold of another CTL-fold containing polypeptide, analogous to the grafting of mouse antibody CDRs onto a human antibody framework. Amino acid residues of the superscaffold may also serve to permit conjugation of the binding protein to another molecule. Thus the superscaffold may be a polypeptide linker as a non-limiting example. The polypeptide linker may be of differing lengths and compositions.

The superscaffold may also optionally constitute or comprise a dimerization or multimerization domain which permits organization of more than one scaffold in three dimensional space without covalent linkage, or optionally through one or more disulfide bonds in addition to non-covalent interactions. Alternatively, the superscaffold may be a linker molecule or linker polypeptide which covalently links a scaffold to another molecule, such as a second scaffold, which may be the same or different from the first scaffold. Additionally, the superscaffold may comprise a transmembrane region or domain capable of tethering the scaffold in a lipid bilayer, such as at a cell surface. Further still, the superscaffold may be another protein molecule to form a fusion protein comprising a scaffold of the invention.

A further aspect of the invention provides additional scaffolds and binding proteins comprising them. Generally, the scaffold is a CTL-fold containing a region with one or more variable residues, which region starts at the end of the β3 strand (or with the last residue thereof) and continues through any intervening secondary structures until, but preferably not including, the non-solvent exposed residues of, or before the start of, the β5 strand. Thus the scaffold may comprise a variable region represented by the sequence -$Xaa_1$-Trp-$Xaa_2$-$Xaa_3$-$Xaa_4$-$Xaa_5$-$Xaa_6$-Ser-$Xaa_7$-$Xaa_8$-Arg-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$- (SEQ ID NO:4) wherein each Xaa is independently any amino acid residue but wherein $Xaa_5$ is preferably Ser, Ala, or Pro, or a conservative substitution of any of these three residues; or $Xaa_7$ is preferably Gly, Ala, or Leu, or a conservative substitution of any of these three residues; and/or $Xaa_8$ is preferably Ser, Tyr, Phe, or Trp, or a conservative substitution of any of these four residues; or SEQ ID NO:4 wherein $Xaa_5$ is Ser or wherein $Xaa_7$ is Gly or wherein $Xaa_8$ is Ser or wherein $Xaa_9$ is Ala or wherein $Xaa_{10}$ is Ala or wherein $Xaa_{12}$ is Trp or wherein $Xaa_{15}$ is Gly or wherein $Xaa_{16}$ is Pro or wherein $Xaa_{17}$ is Ser or wherein $Xaa_{19}$ is Ser or wherein $Xaa_{21}$ is Ala or any combination of the foregoing for $Xaa_5$, $Xaa_7$, $Xaa_8$, $Xaa_9$, $Xaa_{10}$, $Xaa_{12}$, $Xaa_{15}$, $Xaa_{16}$, $Xaa_{17}$, $Xaa_{19}$, and $Xaa_{21}$. The side chains of the Xaa residues in the above sequences form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

At the N terminus, these sequences are optionally extended by all or part of SEQ ID NO:2, wherein the extension may be by 1, 2, 3, 4, 5, or all 6 of the consecutive amino acid residues therein linked to $Xaa_1$ via the carboxyl end of the last Gly residue in SEQ ID NO:2. At the C-terminus, these sequences are also optionally extended by all or part of SEQ ID NO: 3, wherein the extension may be by 1, 2, 3, 4, 5, 6, 7, 8, 9, 10, 11, or all 12 of the consecutive amino acid residues linked to the C terminal Xaa via the amino end of the first Gly residue in SEQ ID NO:3. The sequences may also be extended at both ends by any combination of the above extensions at $Xaa_1$ and $Xaa_{23}$ followed by further optional extensions. Where all 12 amino acids of SEQ ID NO:3 are present, preferred embodiments of the invention have no further extension at the C terminus.

SEQ ID NO:4 containing sequences are preferably part of a scaffold as found in the CTL-fold portion of Mtd. Alternatively, the sequences may be substituted for the corresponding sequence between the β3 and β5 strands of another CTL-fold as described herein.

Alternatively, the scaffold may comprise a cyanobacterium derived variable region represented by -$Xaa_1$-Trp-$Xaa_2$-$Xaa_3$-$Xaa_4$-$Xaa_5$-$Xaa_6$-$Xaa_7$-Cys-Arg-Ser-$Xaa_8$-$Xaa_9$-Arg-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$- (SEQ ID NO:5), optionally with the addition of -$Xaa_{22}$-, or $Xaa_{22}$-$Xaa_{23}$-, or -$Xaa_{22}$-$Xaa_{23}$-$Xaa_{24}$- at the C terminus end, wherein each Xaa is independently any amino acid residue but wherein $Xaa_5$ is preferably Ser, Ala, or Pro, or a conservative substitution of any of these three residues; or $Xaa_8$ is Gly or Ala, or Leu, or a conservative substitution of any of these three residues; and/or $Xaa_9$ is Ser, Tyr, Phe, or Trp, or a conservative substitution of any of these four residues. Again, the side chains of the Xaa residues in the above sequence form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

At the N terminus, these sequences are optionally extended by all or part of SEQ ID NO:2, wherein the extension may be by 1, 2, 3, 4, 5, or all 6 of the consecutive amino acid residues therein linked to $Xaa_1$ via the carboxyl end of the last Gly residue in SEQ ID NO:2. At the C-terminus, these sequences are also optionally extended by all or part of SEQ ID NO: 3, wherein the extension may be by 1, 2, 3, 4, 5, 6, 7, 8, 9, 10, 11, or all 12 of the consecutive amino acid residues linked to the C terminal Xaa via the amino end of the first Gly residue in SEQ ID NO:3. Alternatively, the sequence is extended at the C terminus by all or part of -Gly-Phe-Arg-Leu-Val-Ser-Phe-Pro-Pro-Arg-Thr-Leu-Glu- (SEQ ID NO:6), -Gly-Phe-Arg-Leu-Val-Ser-Phe-Pro-Pro-Arg-Thr-Pro-Glu- (SEQ ID NO:7), -Gly-Phe-Arg-Val-Val-Cys-Ala-Phe-Gly-Arg-Ile-Leu-Gln- (SEQ ID NO:8), or -Gly-Phe-Arg-Val-Val-Cys-Ala-Phe-Gly-Arg-Thr-Phe-Gln- (SEQ ID NO:9), wherein the extension may be by 1, 2, 3, 4, 5, 6, 7, 8, 9, 10, 11, 12 or all 13 of the consecutive amino acid residues in any one of SEQ ID NOs:6-9 linked to the C terminal Xaa via the amino end of the first Gly residue in each SEQ ID NO. The C terminus extension may also be by -Gly-Phe-Arg-Val-Ile-Ser-Ser-Ser-Pro-Val-Val-Ser-Gly-Phe-His-Ser- (SEQ ID NO:10), wherein the extension may be by 1, 2, 3, 4, 5, 6, 7, 8, 9, 10, 11, 12, 13, 14, 15, or all 16 of the consecutive amino acid residues linked to the C terminal Xaa via the amino end of the first Gly residue in SEQ ID NO:10; or by -Gly-Cys-Arg-Val-Val-Val-Val-Arg-Gly-Arg-Leu-Ser- (SEQ ID NO:11), wherein the extension may be by 1, 2, 3, 4, 5, 6, 7, 8, 9, 10, 11, or all 12 of the consecutive amino acid residues linked to the C terminal Xaa via the amino end of the first Gly residue in SEQ ID NO:11.

The sequences may also be extended at both ends by any combination of the above extensions at $Xaa_1$ and $Xaa_{21}$ (or $Xaa_{22}$, $Xaa_{23}$, or $Xaa_{24}$) followed by further optional extensions. Where all the amino acids of any of SEQ ID NOs:3 or 6-11 are present, preferred embodiments of the invention have no further extension at the C terminus.

SEQ ID NO:5 containing sequences are preferably part of a scaffold as found in the CTL-fold of a protein containing a cyanobacterium amino acid sequence as shown in FIG. 5. Those cyanobacterium CTL-fold containing proteins are from *Trichodesmium erythraeum* (preferably T.e. 1A, T.e. 1B, or T.e. 2); *Nostoc* PPC ssp. 7120 (preferably N. PCC. 1, N. PCC. 2A, or N. PCC. 2B); or *Nostoc punctiforme* (preferably N.p. 1 or N.p. 2) and have both protein level homology as well (as indicated in FIG. 5) and genetic similarity because the coding regions for the proteins contain a corresponding TR. Alternatively, the sequences may be substituted for the corresponding sequence between the β3 and β5 strands of another CTL-fold as described herein.

The invention also provides a *Treponema denticola* derived variable region comprising a sequence represented by (SEQ ID NO:12)
-$Xaa_1$-Arg-Val-$Xaa_2$-Arg-Gly-Gly-$Xaa_3$-Trp-$Xaa_4$-$Xaa_5$-$Xaa_6$-Ala-$Xaa_7$-$Xaa_8$-Cys-$Xaa_9$-Val-Gly-$Xaa_{10}$-Arg-$Xaa_{11}$-$Xaa_{12}$-$Xaa_{13}$-$Xaa_{14}$-Pro-$Xaa_{15}$-$Xaa_{16}$-$Xaa_{17}$-$Xaa_{18}$-$Xaa_{19}$-$Xaa_{20}$-Leu-, wherein each Xaa is independently any amino acid residue and the side chains of the Xaa residues in the above sequence form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

The sequence is optionally extended at the C terminus Leu by one or more residues in -Gly-Phe-Arg-Leu-Ala-Cys-Arg-Pro (SEQ ID NO:13) wherein the extension may be by 1, 2, 3, 4, 5, 6, 7, or all 8 of the consecutive amino acid residues linked to the C terminal Leu via the amino end of the first Gly residue in SEQ ID NO:13. Where all 8 amino acids of SEQ ID NO:13 are present, preferred embodiments of the invention have no further extension at the C terminus.

SEQ ID NO:12 containing sequences are preferably part of a scaffold as found in the CTL-fold of a *Treponema denticola* protein containing the corresponding T.d. amino acid sequence in FIG. 5. Alternatively, the sequences may be substituted for the corresponding sequence between the β3 and β5 strands of another CTL-fold as described herein.

The invention further provides a scaffold comprising another phage derived variable region represented by (SEQ ID NO:14)
-Gly-Gly-Gly-Leu-Trp-Cys-Arg-Asn-Tyr-Gly-Asp-Arg-Phe-Pro-Ile-Arg-Gly-Gly-$Xaa_1$-Trp-$Xaa_2$-$Xaa_3$-Gly-Ser-$Xaa_4$-Ala-Gly-Leu-Gly-Ala-Leu-$Xaa_5$-Leu-$Xaa_6$-$Xaa_7$-Ala-Arg-Ser-$Xaa_8$-Ser-$Xaa_9$-$Xaa_{10}$-$Xaa_{11}$-$Xaa_{12}$- wherein each Xaa is independently any amino acid residue and the side chains of the Xaa residues in the above sequence form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

The sequence is optionally extended at the $Xaa_{12}$ end by one or more residues in -Gly-Phe-Arg-Pro-Ala-Phe-Phe-Val (SEQ ID NO:15) wherein the extension may be by 1, 2, 3, 4, 5, 6, 7, or all 8 of the consecutive amino acid residues linked to $Xaa_{12}$ via the amino end of the first Gly residue in SEQ ID NO:15. Where all 8 amino acids of SEQ ID NO:15 are present, preferred embodiments of the invention have no further extension at the C terminus.

SEQ ID NO:14 containing sequences are preferably part of a scaffold as found in the CTL-fold of a *Vibrio* harveyi ML phage protein (ORF35 encoded protein) containing the corresponding V.h. ML amino acid sequence in FIG. 5. Alternatively, the sequences may be substituted for the corresponding sequence between the β3 and β5 strands of another CTL-fold as described herein.

The invention also provides a scaffold comprising a *Bifidobacterium longum* derived variable region represented by (SEQ ID NO:16)

$-Xaa_1$-Arg-Phe-Gly-$Xaa_2$-Leu-$Xaa_3$-$Xaa_4$-Gly-Ala-Ala-

Cys-Gly-Ala-Phe-Ala-Val-$Xaa_5$-Leu-$Xaa_6$-$Xaa_7$-$Xaa_8$-

Leu-Ala-$Xaa_9$-Arg-$Xaa_{10}$-Trp-$Xaa_{11}$-$Xaa_{12}$- wherein each Xaa is independently any amino acid residue and the side chains of the Xaa residues in the above sequence form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

The sequence is optionally extended at the $Xaa_{12}$ end by one or more residues in -Gly-Gly-Arg-Leu-Ser-Ala-Leu-Gly-Arg-Thr-Lys-Ala (SEQ ID NO:17) wherein the extension may be by 1, 2, 3, 4, 5, 6, 7, 8, 9, 10, 11, or all 12 of the consecutive amino acid residues linked to $Xaa_{12}$ via the amino end of the first Gly residue in SEQ ID NO:17. Where all 12 amino acids of SEQ ID NO:17 are present, preferred embodiments of the invention have no further extension at the C terminus.

SEQ ID NO:16 containing sequences are preferably part of a scaffold as found in the CTL-fold of a *Bifidobacterium longum* protein containing the corresponding B.l. amino acid sequence in FIG. 5. Alternatively, the sequences may be substituted for the corresponding sequence between the β3 and β5 strands of another CTL-fold as described herein.

Additionally, the invention also provides a scaffold comprising a *Bacteroides thetaiotaonicron* derived variable region represented by (SEQ ID NO:18)

$-Xaa_1$-Gly-$Xaa_2$-Cys-Trp-Ser-Ala-Val-Pro-$Xaa_3$-$Xaa_4$-

$Xaa_5$-$Xaa_6$-$Xaa_7$-Gly-$Xaa_8$-$Xaa_9$-Leu-$Xaa_{10}$-Phe-$Xaa_{11}$

Ser-Ser-$Xaa_{12}$-Val-$Xaa_{13}$-Pro-Leu-$Xaa_{14}$-$Xaa_{15}$-$Xaa_{16}$-

$Xaa_{17}$- wherein each Xaa is independently any amino acid residue and the side chains of the Xaa residues in the above sequence form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

The sequence is optionally extended at the $Xaa_{17}$ end by one or more residues in -Arg-Ala-Cys-Gly-Phe-Gly-Leu-Arg-Ser-Ser-Gln-Glu (SEQ ID NO:19) wherein the extension may be by 1, 2, 3, 4, 5, 6, 7, 8, 9, 10, 11, or all 12 of the consecutive amino acid residues linked to $Xaa_{17}$ via the amino end of the first Arg residue in SEQ ID NO:19. Where all 12 amino acids of SEQ ID NO:19 are present, preferred embodiments of the invention have no further extension at the C terminus.

SEQ ID NO:18 containing sequences are preferably part of a scaffold as found in the CTL-fold of a *Bacteroides thetaiotaonicron* protein containing the corresponding B.t. amino acid sequence in FIG. 5. Alternatively, the sequences may be substituted for the corresponding sequence between the β3 and β5 strands of another CTL-fold as described herein.

Additionally, the invention provides for the use of the region between the β3 and β5 strands of a CTL-fold as a variable region in which amino acids may be altered to produce novel binding sites with different specificities and avidities. Thus in an additional aspect of the invention, the nucleic acid sequence encoding the CTL-fold of a CTL-fold containing protein may be operably linked to a template region (TR), and an IMH as needed, wherein the TR corresponds to all or part of the binding site in the CTL-fold and contains adenine residues that direct changes in the amino acid sequence of the binding site, and thus variable region, as described herein. Preferred embodiments of the invention include CTL-fold encoding nucleic acids with the Mtd IMEl, or a functional fragment thereof, to direct alterations in the VR based on adenine residues in the functionally linked TR.

A scaffold in a binding protein of the invention is preferably all or part of a CTL-fold that correctly orients the binding site contained therein. Non-limiting examples of CTL-folds include that in Mtd as described herein as well those classified as C-type lectin-like domains (CTLDs) and divergent CTLDs. Preferred regions of the CTL-fold in Mtd are residues 171-381 and residues 306-381 of SEQ ID NO:20. In the case of residues 171-381, the size is analogous to recombinant single chain antibodies composed of a single variable domain (VHH), which remains a stable polypeptide with the antigen binding capability of the original variable region of the heavy chain (see Nanobodies™ by Ablynx). These VHH are based on antibodies that lack light chains found in camelidae (camels and llamas). In the case of residues 306-381, at least one region composed of residues 171-199, residues 237-263, residues 200-236, or residues 264-305 is preferably present in the fold as well. Particularly preferred is the presence of any two, any three, or all four of these regions.

CTLD examples include those that bind $Ca^{2+}$, such as carbohydrate recognition domains (CRDs), C-type lectin domains (which bind sugars), coagulation factor binding proteins, and IgE Fc receptor. Divergent CTLD examples include type II antifreeze proteins, oxidized LDL receptor, phospholipase receptors, NK cell receptors (which bind MHC ligands). Other non-limiting examples include link protein modules, endostatin, and intimin. For a review of the C-type lectin fold, see Drickamer, K. "C-type lectin-like domains." *Curr Opin Struct Biol* 9, 585-90 (1999).

Preferably, the CTL-fold is bacterial (including bacterial phages), human or mammalian in origin. Non-limiting examples include the selectins (see Lasky (1995) *Annu. Rev. Biochem.,* 64:113-139), including E-selectin, L-selectin and P-selectin; mannose binding protein (MBP), including MBP-A and MBP-C; the natural killer (NK) receptor NKG2D; CD69; eosinophilic major basic protein (EMBP); tumour necrosis factor-stimulated gene-6 product (TSG-6); enteropathogenic *E. coli* (EPEC) intimin (the D3 domain therein is a CTL-fold); and *Yersinia pseudotuberculosis* invasin (the D5 domain is a CTL-fold).

An MBP derived variable region of the invention is represented by

-$Xaa_1$-$Xaa_2$-Gly-$Xaa_3$-Trp-Asn-Asp-$Xaa_4$-$Xaa_5$-Cys-$Xaa_6$-$Xaa_7$-$Xaa_8$- (SEQ ID NO:21) wherein each Xaa is independently any amino acid residue; or SEQ ID NO:21 wherein $Xaa_1$ is Asp or wherein $Xaa_2$ is Asn or wherein $Xaa_3$ is Leu, Gln, His, or Lys or wherein $Xaa_4$ is Ile, Val, or Asp or wherein $Xaa_5$ is Ser, Pro, Val, or Ala or wherein $Xaa_6$ is Gln, Asn, Arg, or His or wherein $Xaa_7$ is Ala, Tyr, Arg, or Lys or wherein $Xaa_8$ is Ser, Gln, Pro, or Arg or any combination of the foregoing for $Xaa_1$ to $Xaa_8$.

The side chains of the Xaa residues in the above sequences form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

SEQ ID NO:21 containing sequences are preferably part of a scaffold as found in the CTL-fold of an MBP protein, preferably with a collagenous domain. Alternatively, the sequences may be substituted for the corresponding sequence between the β3 and β5 strands of another CTL-fold as described herein.

A selectin derived variable region of the invention is represented by

-$Xaa_1$-$Xaa_2$-$Xaa_3$-$Xaa_4$-$Xaa_5$-$Xaa_6$-$Xaa_7$-Gly-$Xaa_8$-Trp-Asn-Asp-$Xaa_9$-$Xaa_{10}$-Cys-$Xaa_{11}$-$Xaa_{12}$-$Xaa_{13}$- (SEQ ID NO:22) wherein each Xaa is independently any amino acid residue; or SEQ ID NO:22 wherein $Xaa_1$ is Ile or wherein $Xaa_2$ is Lys or wherein $Xaa_3$ is Arg or wherein $Xaa_4$ is Gln or wherein $Xaa_5$ is Arg or wherein $Xaa_6$ is Asp or wherein $Xaa_7$ is Ser or wherein $Xaa_8$ is Leu, Gln, His, or Lys or wherein $Xaa_9$ is Ile, Val, or Asp or wherein $Xaa_{10}$ is Ser, Pro, Val, or Ala or wherein $Xaa_{11}$ is Gln, Asn, Arg, or His or wherein $Xaa_{12}$ is Ala, Tyr, Arg, or Lys or wherein $Xaa_{13}$ is Ser, Gln, Pro, or Arg or any combination of the foregoing for $Xaa_1$ to $Xaa_{13}$.

The side chains of the Xaa residues in the above sequences form a binding site, in whole or in part. At each of the N and C terminal ends of the sequences are optional amino acid sequences, or one of the ends is —H (a covalently bonded hydrogen atom), such as those that form a CTL-fold containing the binding site displayed in a solvent exposed portion of the fold.

SEQ ID NO:22 containing sequences are preferably part of a scaffold as found in the CTL-fold of a selectin protein. Alternatively, the sequences may be substituted for the corresponding sequence between the β3 and β5 strands of another CTL-fold as described herein.

In a further aspect, the invention provides nucleic acid molecules, or polynucleotides, encoding the scaffolds and binding proteins as described herein. The nucleic acids or polynucleotides may be part of a nucleic acid vector or plasmid, optionally in a cell, preferably suitable for expression of the encoded protein. The scaffold is preferably all or part of a variable region (VR) in the nucleic acid molecule which is operably linked to an initiation of mutagenic homing (IMH) sequence and a template region (TR) as described below. Thus nucleic acid molecules encoding the CTL-folds described above, but which do not have an operably linked IMH and/or TR components, may be modified to be a nucleic acid molecule of the invention by attachment of the necessary functional nucleic acid components.

The invention also provides a plurality, or library, of scaffolds or binding proteins as well as methods for their production. Thus, a method of producing a plurality of scaffolds or proteins with different binding specificities is disclosed, the method comprising expressing and replicating a nucleic acid molecule or polypeptide encoding a scaffold or binding protein of the invention in a cell under conditions of mutagenic homing wherein said TR directs mutagenesis of variable residues within the variable region (VR) containing the scaffold. Non-limiting examples of a plurality or library of scaffolds or binding proteins include those expressed as a phage display, ribosome display, polysome display, or cell surface display as well as those presented as an array or microarray format. In some preferred embodiments, the plurality is expressed as part of the tail fibers of *Bordetella* bacteriophages.

The resultant plurality or library of scaffolds or binding proteins may be screened for binding against a target molecule of interest. The invention provides a method of selecting for binding comprising producing or providing a plurality, or library, of scaffolds or proteins in a plurality of cells as described above followed by selecting proteins which bind a molecule of interest after individually contacting each of said plurality of scaffolds or proteins (or phage particles, cells, or media containing them) with a target molecule of interest. Optionally, the binding proteins in the plurality or library are in dimeric or other multimeric form. The invention also provides for identifying a multimeric form of a binding protein as having a greater avidity for the target molecule of interest than a monomeric form of the protein.

Alternatively, the plurality or library of scaffolds or binding proteins may be screened for binding to any one of a multiplicity of target molecules as an additional method of the invention. The scaffolds or proteins contacted with multiple molecules followed by selection of those scaffolds or proteins that bind at least one of the target molecules may be isolated. The multiple target molecules may be in a mixture or disposed on an array or microarray as non-limiting examples. Other such examples include multiple molecules in or on a cell or tissue as well as multiple molecules immobilized on a solid support. The target molecules are preferably polypeptides, optionally modified by glycosylation, phosphorylation, or other post-translational modification; carbohydrates; lipids; or complex combinations thereof. The target molecules may be expressed on the exterior of phage or a virus, or a viable or non-viable cell of any phyla. In some embodiments of the invention, the plurality or library of scaffold or binding protein is expressed on the exterior of phage, such as *Bordetella* bacteriophage.

Where the members of a plurality or library of scaffolds or binding proteins are individually expressed on the exterior of individual phage particles, the invention provides methods of selecting for binding against a target ligand or molecule of interest by use of the plurality or library of phage particles. The plurality, or library, is provided and contacted with a target ligand or molecule of interest followed by selection of phage which bind the ligand or molecule, optionally by removal of phage which do not bind. The selected phage particles may be propagated followed by one or more additional rounds of contacting and selection, optionally under more stringent wash conditions, to "enrich" for phage expressing a scaffold or binding protein with greater affinity or avidity. The polynucleotide encoding the scaffold or binding protein may be isolated from the selected phage and analyzed (e.g. sequenced), amplified or propagated to produce the scaffold or binding protein. In cases of a binding protein, the phage may have been expressing the protein in dimeric, trimeric or other multimeric form. Such selected phage may be used as sources of genes or gene fragments encoding binding protein molecules with the desired specificity and avidity.

The selection methods of the invention may further include an additional determination of the scaffold or binding proteins, selected as described above, as binding or not binding to a second molecule. Scaffolds or binding proteins that bind a second molecule would be identified as non-specific for the target ligand or molecule of interest, while those that do not bind a second molecule would be identified as specific for the target ligand or molecule of interest relative to the second molecule.

The scaffolds and binding proteins of the invention may also be modified, such as by attachment of another moiety thereto. Non-limiting examples of a moiety for attachment include a detectable label or a toxin or activatable pro-drug. Modified scaffolds and binding proteins may be used to target a cell which is bound thereby. As a non-limiting example, a detectably labeled modified scaffold or binding protein may be used to detect a cell expressing a molecule bound by the binding site of the scaffold or protein. The molecule may be expressed on the cell surface, such that the scaffold or binding protein binds the exterior of the cell. The molecule may also be expressed within the cell, wherein the scaffold or binding protein binds after introduction into the interior of the cell, such as, but not limited to, cases where the cells have been permeabilized. Non-limiting examples of cells that may be detected include both prokaryotic and eukaryotic cells, including bacterial cells and higher eukaryotic cells from a multicellular organism.

A modified scaffold or binding protein attached to a toxin, or pro-drug form thereof, may be used to decrease the viability of, or to kill, cells which express a cell surface molecule bound by the modified scaffold or protein. Preferably, the cells are cancer cells, such as those of a mammal, preferably a human.

In additional aspects of the invention, compositions comprising the scaffolds and binding proteins of the invention are provided. The compositions may be used for the practice of the methods disclosed herein, including diagnostic, prophylactic or therapeutic applications. Additionally, compositions comprising the nucleic acid molecules and polypeptides disclosed herein as well as materials for the expression thereof are provided. These compositions may be provided in the form of a kit for the expression and production of the scaffolds and proteins of the invention.

The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

7120 #2B (N. PCC. 2B); *Nostoc punctiforme* #1 (N.p. 1); and *Nostoc punctiforme* #2 (N.p. 2).

DETAILED DESCRIPTION OF MODES OF PRACTICING THE INVENTION

This invention is based in part on X-ray crystal structures of four Mtd variants, each competent to promote infectivity and each having a different receptor specificity (Mtd-P1, -3c, -M1, and I1). The structure of a fifth Mtd variant from a non-infective phage (see Mtd-N1 in FIG. 1) was also determined. The 1.5 Å resolution structure of Mtd-P1 was determined by multiwavelength anomalous dispersion using seleno-methionine substituted protein, and structures of other Mtd variants were determined by molecular replacement. The overall structures of these variants are nearly identical, indicating sequence variation within the VR causes no large conformational shifts.

Figure 2A:
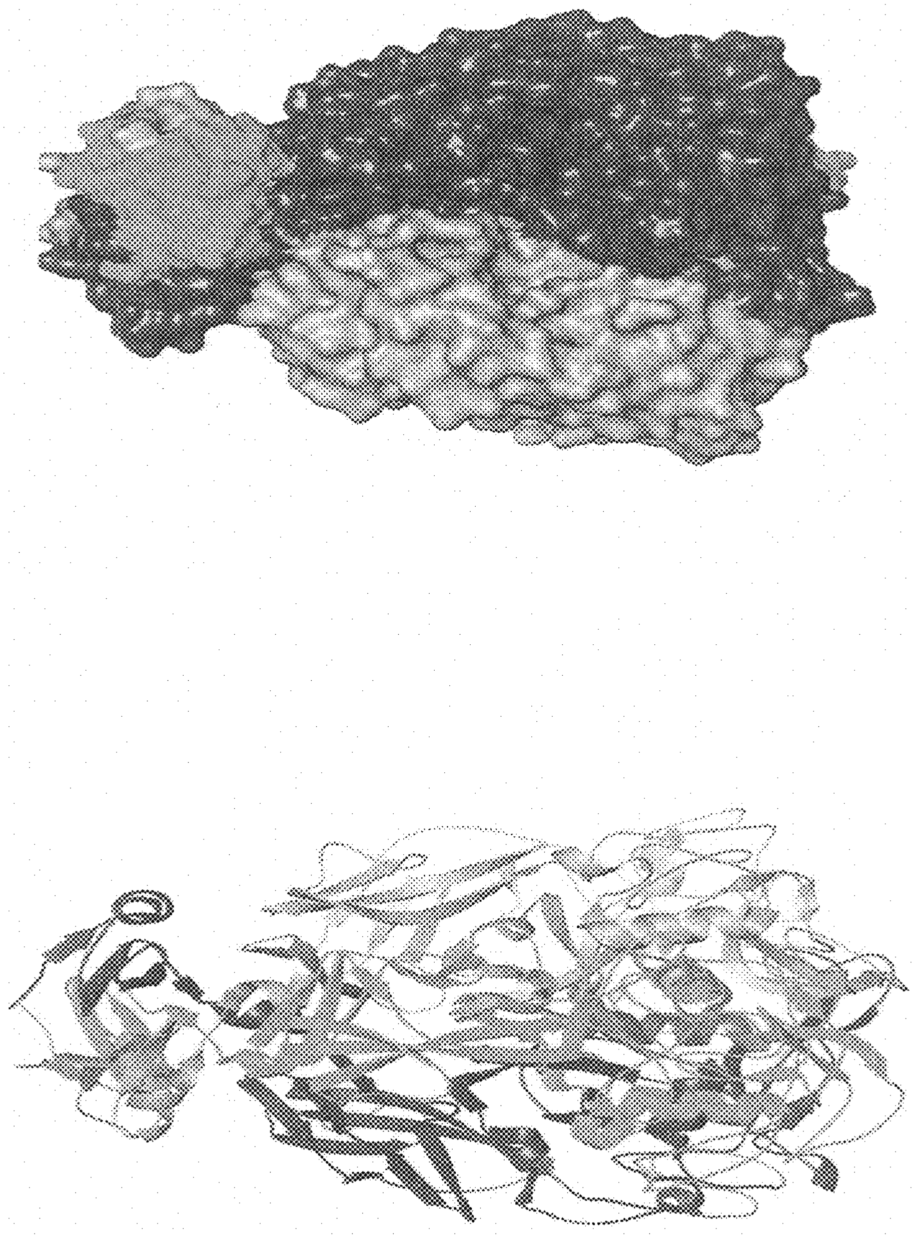
FIG. 2A shows two representations of the intertwined, pyramid-shaped trimer structure of several Mtd variants.

The Mtd variants are all seen to form an intertwined, pyramid-shaped trimer (FIG. 2A). The dimensions of the trimer (height and base of ~90 Å and ~50 Å, respectively) correspond roughly to the size of knobs seen on the ends of *Bordetella* phage tail fibers (see Liu, M. et al. Genomic and genetic analysis of *Bordetella* bacteriophages encoding reverse transcriptase-mediated tropism-switching cassettes. *J Bacteriol* 186, 1503-17 (2004)). The extensive trimer interface buries more than 4,500 $Å^2$ of surface area in each monomer, consistent with an obligatory trimer and with trimeric association observed by static light scattering. The majority (69%) of the interface area is composed of non-polar residues. Each polypeptide is also joined to its neighbor via 20 hydrogen bonds, one electrostatic interaction (between Glu-234 and Arg-354), and at least one shared cation (magnesium or calcium at Phe-313 carbonyl).

Figure 2B:
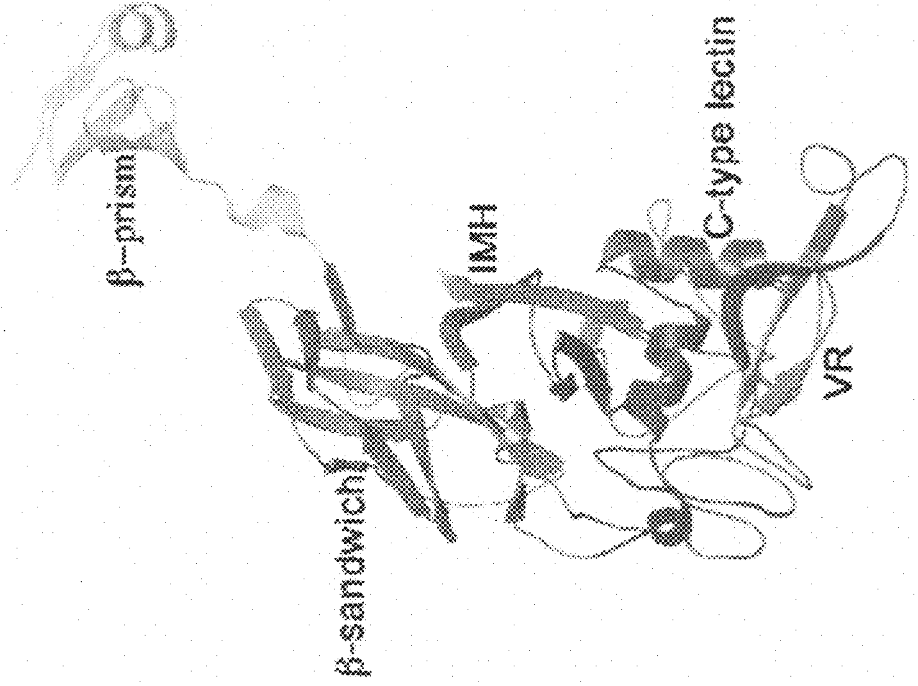
FIG. 2B shows a representation of an Mtd monomer and three domains therein: β-prism, intermediate domain containing the β-sandwich, and C-type lectin (CTL)-fold including the VR and the region corresponding to the IMH.
Figure 2C:
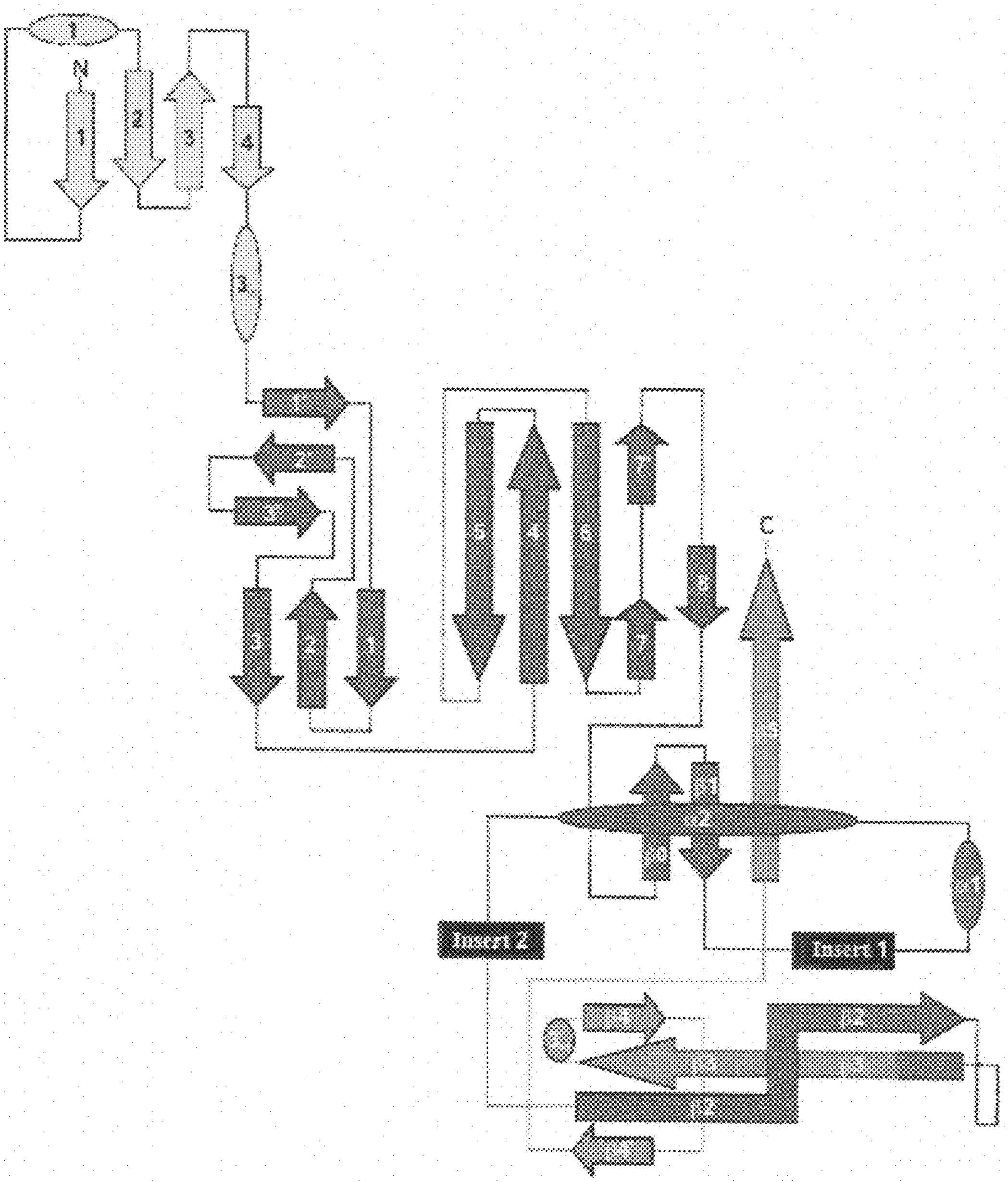
FIG. 2C is a schematic showing regions of secondary structure in Mtd.

Mtd is composed of three domains (see FIG. 2B). At the apex of the pyramid, the N-terminal domains (residues 1-48) of each of the three monomers form a threefold symmetric β-prism, with each monomer contributing a four-stranded, antiparallel β-sheet flanked by a short α-helix. The β-prism is structurally similar to the pseudo-threefold symmetric β-prisms observed in monocot lectins (rmsd 2.4 Å, 60 Cα atoms, see Hester, G., Kaku, H., et al. Structure of mannose-specific snowdrop (*Galanthus nivalis*) lectin is representative of a new plant lectin family. *Nat Struct Biol* 2, 472-9 (1995)). However, the Mtd β-prism does not contain the spatial arrangement of residues required in monocot lectins which bind carbohydrates without a CTL-fold.

The β-prism domain of each Mtd monomer is joined to the following intermediate domain by a short $3_{10}$-helix (residues 49-54), which intertwines with equivalent $3_{10}$-helices from other monomers. These connections cross such that the β-prism domain occupies a different face of the pyramid than the other domains.

In contrast to the intimate trimeric association of the β-prism domain, the intermediate domain (residues 56-170) splays away from the trimer axis and makes little contact to other monomers. The intermediate domain is formed by an elaborated β-sandwich containing three- and four-stranded antiparallel sheets and with the three-stranded sheet making a near right-angle turn near its middle (see FIG. 2B). The structure of the intermediate domain appears to constitute a novel fold. Without being bound by theory, and offered to advance understanding of the invention, the N-terminal β-prism or intermediate β-sandwich domains are theorized to permit association of the individual monomers with each other as well as being possibly involved in tethering Mtd to the surface of *Bordetella* phage.

The superscaffold of the proteins of the invention may thus include all or part of one or both of the β-prism and intermediate domains of Mtd, where the Mtd CTL-fold contains one scaffold of the invention. These superscaffold domains may be used to arrange and display the binding site of a scaffold of the invention as described herein.

The Mtd C-terminal domain (residues 171-381), which constitutes more than half of Mtd and contains the VR, is unexpectedly found to have a C-type lectin (CTL)-fold (see Weis, W. I., et al. Structure of the calcium-dependent lectin domain from a rat mannose-binding protein determined by MAD phasing. *Science* 254, 1608-15 (1991); Drickamer, K. C-type lectin-like domains. *Curr Opin Struct Biol* 9, 585-90 (1999); and Holm, L. et al. Protein structure comparison by alignment of distance matrices. *J Mol Biol* 233, 123-38. (1993)). See FIG. 3A. Although originally named for calcium-dependent carbohydrate binding in mammalian mannose binding protein (MMBP, see Weis, W. I., et al. Structure of a C-type mannose-binding protein complexed with an oligosaccharide. *Nature* 360, 127-34 (1992)), different individual CTL-folds have been recognized to bind different ligands.

The similarity of Mtd to carbohydrate-binding CTL proteins, such as MMBP (1.5 Å rmsd, 60 Cα atoms), appears to be the result of convergent evolution. None of the 14 residues absolutely conserved in carbohydrate-binding CTL domains is found in Mtd, and neither are the residues required for calcium- and carbohydrate-binding. Likewise, none of the four disulfide-bond forming cysteines found in many CTL domains is found in Mtd, confirming that disulfides are not required for stability of CTL-folds. Furthermore, Mtd has no obvious amino acid sequence relationship to other convergently evolved CTL domains, such as the *E. coli* virulence factor intimin, but does have structural similarity as expected (rmsd 1.8 Å, 75 Cα atoms).

Figure 3A:
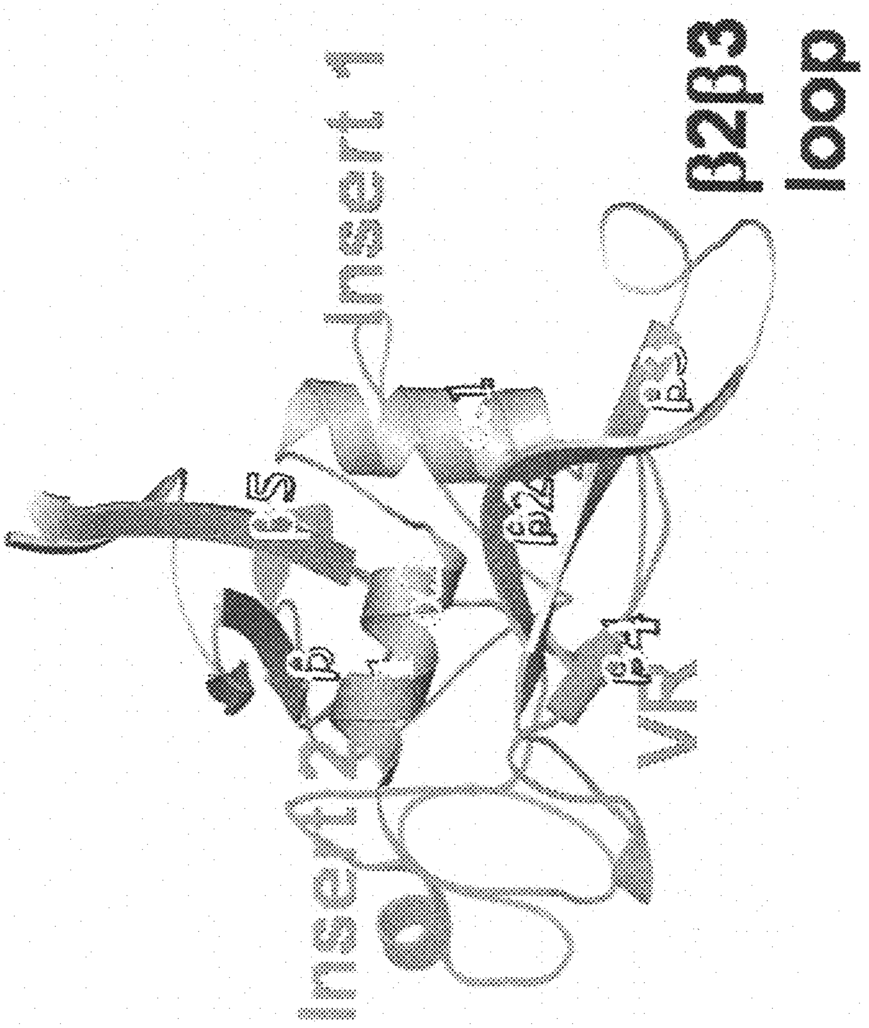
FIG. 3A shows a representation of an Mtd CTL-fold.

The typical distinguishing features of the ~110-130 residue CTL-fold, as also seen in Mtd, are a two-stranded antiparallel β-sheet formed by the domain's N- and C-termini (β1β5) connected by two β-helices to a three-stranded, antiparallel β-sheet (β2β3β4), see FIG. 3A. These features are also generally present in other CTL-folds, which range from about 95 to about 150 residues, described herein for use in the practice of the invention. The β2 strand is uniquely twisted in Mtd such that it crosses over the β3 strand. Unique to Mtd are inserts (residues 200-236 and 264-305) that interrupt connections between β1 and α1 and between α2 and β2, respectively, as well as some additional short strands (β0 and β4'). The inserts have no regular secondary structure but do have specific conformations due to an extensive hydrogen bonding network, including to residues within the binding site. Without being bound by theory, and offered to advance the understanding of the present invention, it is possible that the inserts stabilize the VR as discussed below. As noted above, the Mtd CTL-fold, and other analogous CTL-folds of similar structural arrangement, may be used as a scaffold in the practice of the present invention.

Figure 3B:
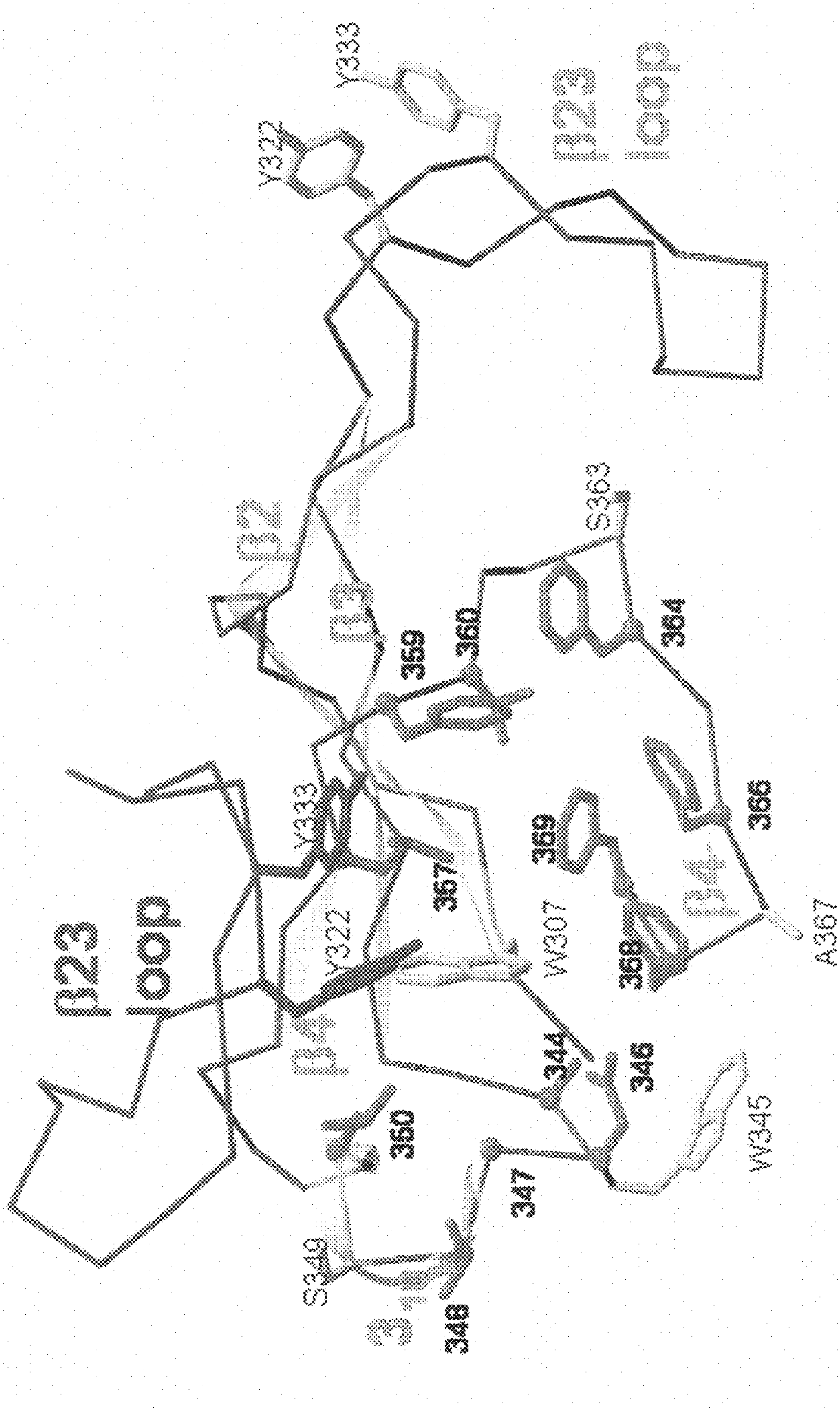
FIG. 3B shows a representation of 12 variable residues which are almost all solvent-exposed and organized into a receptor-binding site on the external face of the Mtd β2β3β4β4' sheet.

The Mtd CTL-fold contains 12 residues that are variable. The 12 variable residues are almost all solvent-exposed and organized into a receptor-binding site on the external face of the β2β3β4β4' sheet (FIG. 3B). This face is equivalent to the one in the CTL-fold proteins Ly49A (see Tormo, J., et al. Crystal structure of a lectin-like natural killer cell receptor bound to its MHC class I ligand. *Nature* 402, 623-31 (1999)) and intimin (Luo, Y. et al. Crystal structure of enteropathogenic *Escherichia coli* intimin-receptor complex. *Nature* 405, 1073-7 (2000); and Batchelor, M. et al. Structural basis for recognition of the translocated intimin receptor (Tir) by intimin from enteropathogenic *Escherichia coli*. *EMBO J* 19, 2452-64 (2000)) responsible for interaction with their respective targets, class I MHC molecules and Tir. Half of the 12 variable residues are located on regular secondary structure elements: three are located on β-strands (357 on β4; 368 and 369 on β4'), and three on a $3_{10}$-helix that connects β3 to β4 (347, 348, and 350), see FIG. 3B. The other half of the variable residues occupy loop positions preceding the $3_{10}$-helix (344 and 346) or connecting β4 to β4' (359, 360, 364, and 366).

All variable residues, except for 348 and 369, are encoded by AAC codons in TR. Adenine-directed mutagenesis permits substitution of Asn encoded by AAC with 14 other residues, which cover the gamut of chemical character. For example, while adenine substitution of AAC cannot produce a codon for Trp, it can produce codons for Phe and Tyr. Likewise, while substitution cannot produce codons for Glu and Lys, it can produce codons for Asp and Arg (also His). Significantly, the use of the AAC codon rules out a nonsense codon being introduced. Adenine-substitution of the two non-AAC codons in TR, ACG encoding Thr-348 and ATC encoding Ile-369, can produce three other amino acids (Ser, Pro, Ala at 348; Val, Leu, Phe at 369). There appears to be no structural necessity for residue 348 to be small, but 369 is preferably hydrophobic to pack between the invariant residues Trp-307 and Trp-309 (FIG. 3B).

Along with these variable residues, the binding site in Mtd contains four invariant, solvent-exposed aromatic residues that are likely to contribute to interactions despite their status as amino acid residues of a scaffold as described herein. These are Trp-307 and Trp-345 at the center and periphery, respectively, of the binding site. Also at the periphery are the invariant residues Tyr-322 and Tyr-333, which come from the intertwining of an adjacent monomer's β2β3 loop into a neighbor's binding site (FIG. 3B). Altogether, the binding site including the variable and above invariant residues in Mtd-P1 presents ~900 $Å^2$ of exposed surface area.

In the practice of the invention, it is contemplated that "conservative amino acid substitutions" may be favored due to the interchangeability of residues having similar side chains. Thus amino acids may be grouped based upon the similarities of their side chains and substituted for each other on this basis. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. The invention provides for the "conservative substitution" of one amino acid residue in a group by another amino acid residue in the same group. Other conservative amino acid substitution groups include, but are not limited to, valine-leucine-isoleucine, phenylalanine-tyrosine, lysine-arginine, alanine-valine, and asparagine-glutamine.

The final portion of VR, the β5 strand, is encoded by the 'initiation of mutagenic homing' (IMH) sequence, which maintains the unidirectional flow of mutagenized genetic information from TR to VR. This region of VR is unaffected by adenine-directed mutagenesis and therefore invariant. Invariance at the nucleotide level is echoed at the protein level among Mtd variants, with β5 making close intra- and inter-molecular contacts within the central core of the trimer that would be potentially disrupted by variation. Thus all or part of this IMH-encoded β5 strand of the protein may be part of a superscaffold as described herein while the nucleic acid encoding the β5 strand, or a portion thereof, serves as the IMH, which maintains the unidirectional flow of diversity generating information from TR to VR.

Based in part on the foregoing, the present invention provides a binding protein comprising a scaffold for presentation of a binding site with variable residues as described herein. In a broad sense, the scaffolds and binding proteins of the invention may be substituted for antibodies, and antigen binding fragments thereof, or other affinity agents in detection or other affinity-based assays or in therapeutics as known in the art.

In preferred embodiments, the scaffold comprises all or part of a CTLD, the Mtd CTL-fold, or an Mtd-like CTL-fold. In the case of the Mtd CTL-fold, the scaffold would permit possible variation at one or more of the 12 variable residues described herein. Alternatively, the scaffold comprises all or part of another CTL-fold, including those of microbial proteins as described herein (see FIG. 5 and Example 3) as well as those of a selectin; MBP; NKG2D; CD69; EMBP; TSG-6; and intimin as described herein. By "binding site", it is meant the side chains of variable residues which define, in whole or in part, the three dimensional structure or shape which permits binding of the polypeptide attached to the side chains (through the alpha carbons of each variable residue) to a target molecule. Thus a scaffold is a polypeptide which functionally presents the binding site defining variable residues (contained in said polypeptide) to interact with a target molecule bound by the binding site. Scaffolds of the invention that contain a binding site that is functionally presented to bind a target molecule are thus analogous to a Fv region of an antibody molecule and so may be used in analogous ways. As a non-limiting example, a scaffold of the invention may be conjugated to another molecule as described herein, such as to form a fusion protein or to form a labeled scaffold. The scaffolds of the invention may also be viewed as comprising a variable region which contains a binding site of the invention.

The relationship between a binding site, and thus a scaffold or binding protein of the invention, and a "target molecule" as used herein may also be described as the relationship between the members of a binding pair, wherein one member of the pair has an area on its surface or in a portion thereof which binds to the other member of the pair. The relationship may also be described as that between members of a specific binding pair, wherein one member of the pair has an area on its surface or in a portion thereof which specifically binds to the other member of the pair. The members of a pair may be referred to as ligand and anti-ligand (or ligand and receptor), either of which may be the scaffold or binding protein of the invention. The members of a pair are exemplified by other known, and non-limiting examples, including antibody and antigen or hapten; biotin and avidin (or streptavidin); hormone and hormone receptor; immunoglobulin and protein A; and phosphorylated serine residues and annexin. Thus a scaffold or binding protein of the invention may be viewed as a receptor that binds a ligand as the molecule of interest, or as a ligand that is bound by a receptor as the molecule of interest.

Preferably, a scaffold of the invention is at least about 40 amino acid residues. The scaffold may also be about 45, about 50, about 55, about 60, about 65, about 70, about 75, about 80, about 85, about 90, about 100, about 110, about 120, about 130, about 140, about 150, about 160, about 170, about 180, about 190, about 200, about 220, or about 230 or more amino acid residues.

The scaffold in a binding protein of the invention is also preferably in the C-terminal half of the protein. More preferred is where the scaffold is within about 100, about 75, about 50, about 40, about 30, about 20, or about 10 amino acid residues of the C-terminus of the protein.

Scaffolds containing a binding site may also be conjugated to a superscaffold as described herein to form a binding protein of the invention. A superscaffold of the invention of course does not interfere with the presentation of the binding site by the scaffold, although as explained herein, the superscaffold can serve to permit multimerization of scaffolds, and thus multimerization of binding sites in order to effect high avidity of the binding site comprised of multiple identical or non-identical lower affinity binding sites. Alternatively, the superscaffold can serve as a means, or a linker, to permit conjugation of another molecule to the scaffold and thus binding site through the structure of the superscaffold.

The amino acid sequences that form the superscaffold are preferably those of non-CTL-fold regions naturally occurring in association with a CTL-fold. One non-limiting example is residues 1-170 of Mtd (SEQ ID NO:20). Other non-limiting examples include the oligomerization domains described by Drickamer (Ibid), including α-helical domains of mannose-binding protein (MBP), which domains form trimeric coiled coils; the β strand from the N terminus of the MBP CRD, optionally with the C-terminal β strand of the CRD and the C-terminal end of helix α2, which dimerize MBP when the α-helical coiled coil domain is absent; the N-terminal β strands of the Polyandrocarpa lectin, optionally with helix α2; loops from factors IX and X which permit the formation of a "head to head" interaction between two CTLDs with optional stabilization by an interchain disulfide bond. Of course the resultant multimers may be homomultimers, composed of scaffolds with the same binding activity, or heteromultimers, composed of scaffolds with more than one binding activity. Thus the invention provides for homodimers, heterodimers, homotrimers, heterotrimers, as well has higher orders of homomeric and heteromeric proteins. Further non-limiting examples include the transmembrane and domains D0, D1, and/or D2 of EPEC intimin as well as the four Ig-like domains (D1-D4) of *Y. pseudotuberculosis* invasin.

The binding proteins of the invention are thus made up of at least a scaffold containing a binding site as described herein. This combination may be non-naturally occurring in the sense that the binding site may be part of a variable region derived from a first CTL-fold that is inserted into the corresponding region of a second, and different, CTL-fold. Thus, as a non-limiting example, the Mtd based binding site may be inserted in place of the corresponding region between the β3 and β5 strands of another CTL-fold as described herein. The binding proteins of the invention may thus be considered "recombinant". Additional "recombinant" binding proteins include those comprising a superscaffold attached to the scaffold wherein the superscaffold is not derived from the same protein as the scaffold. The polypeptide sequence of the superscaffold is preferably that attached to a CTL-fold containing protein described herein. Further "recombinant" binding proteins include the multimeric forms of a superscaffold containing binding protein wherein the subunits of the multimeric form may be the same (to result in a homomultimer) or different (to result in a heteromultimer).

Preferably, a scaffold or binding protein of the invention is not an isolated form of a naturally occurring polypeptide, where isolated refers to a state of being substantially removed from, preferably entirely removed from, other polypeptides or biomolecules that are normally found with a naturally occurring polypeptide. A naturally occurring polypeptide is one produced by a living organism in the absence of manipulation or modification by human intervention. Non-limiting examples of human intervention include recombinant DNA methodology, mutagenesis by chemical or physical means, inhibition of DNA repair, or manipulation of genetics. Stated differently, the binding proteins of the invention are preferably recombinant proteins or otherwise the result of human intervention. Thus a scaffold or binding protein produced by the recombinant methods described herein, is not a naturally occurring polypeptide.

The term "recombinant" refers to the alteration of a native nucleic acid, or protein or modification by the introduction of a heterologous nucleic acid or protein, via human intervention. The term may refer to a cell derived from a cell so modified. As a non-limiting example, recombinant cells express genes that are not found within the native (nonrecombinant) form of the cell or express native genes in an unnaturally overexpressed, under-expressed, or not expressed state.

Figure 5:
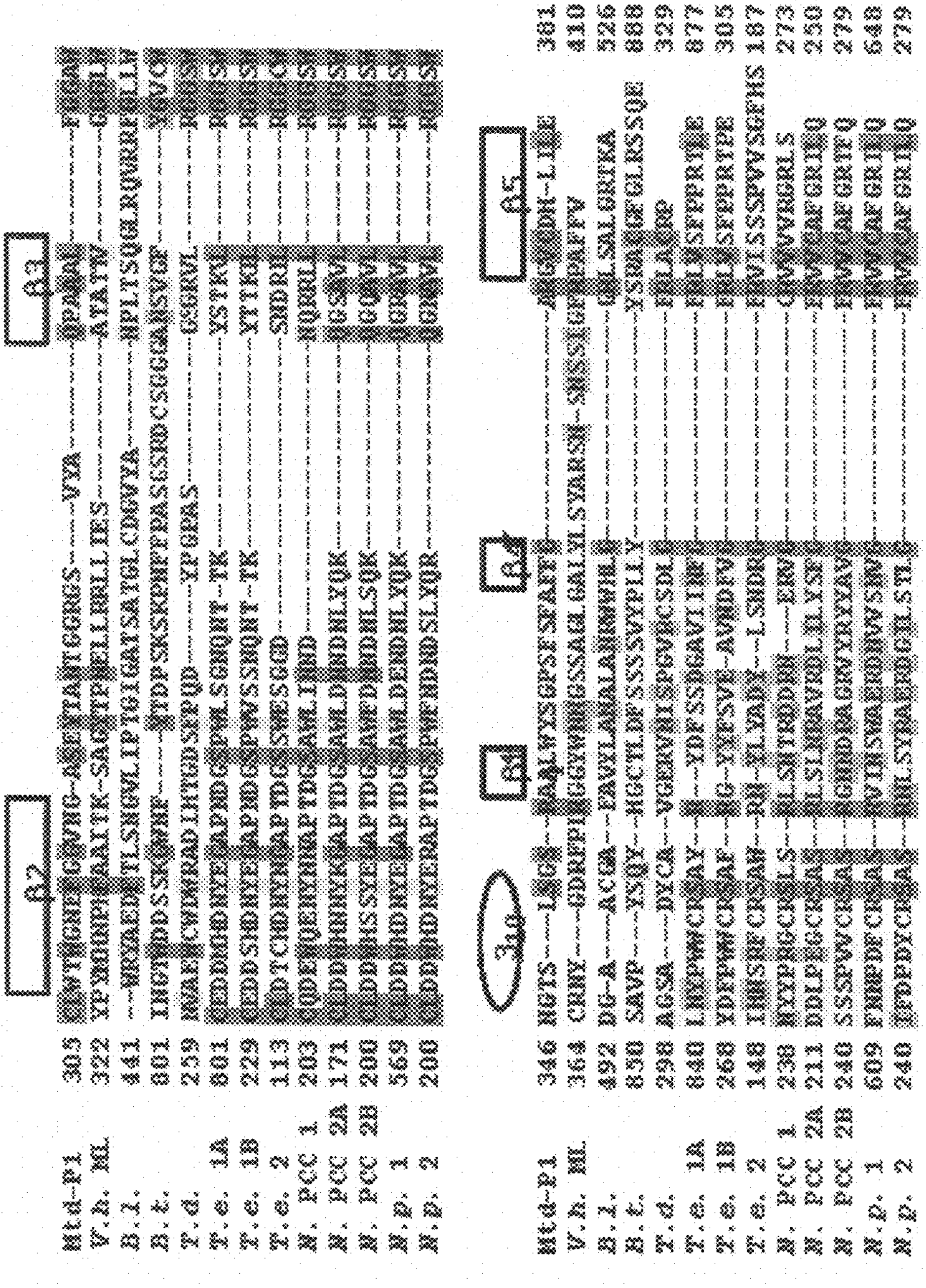
FIG. 5 shows the structure-based sequence alignment of the β2β3β4β4' sheet of the CTL-fold in Mtd-P1 and 12 variable proteins of putative DGRs, (SEQ ID NOS:33-45), as discussed herein. Residues colored light gray correspond to variable residues in Mtd, and those residues found to differ between VR and TR in genomic sequences of the other 12 proteins. Residues colored dark gray are those that could vary by an adenine-directed mechanism in these other proteins. Magenta corresponds to identical residues and yellow to residues conserved in chemical character. In assigning color, the grays take precedence over magenta and yellow, such that certain putatively variable residues are also identical or conserved. Secondary structure elements (box for β-strand, and oval for $3_{10}$-helix) for Mtd are denoted above the alignment, and the 'GGXW' motif is also denoted. The 12 variable proteins of putative DGR's (SEQ ID NOS:34-45) are from *Vibrio harveyi* ML phage (V.h. ML); *Bifidobacterium longum* (B.l.); *Bacteroides thetaiotaonicron* (B.t.); *Treponema denticola* (T.d.); *Trichodesmium erythraeum* 1A (T.e. 1A); *Trichodesmium erythraeum* 1B (T.e. 1B); *Trichodesmium erythraeum* #2 (T.e. 2); *Nostoc* PPC ssp. 7120 #1 (N. PCC. 1); *Nostoc* PPC ssp. 7120 #2A (N. PCC. 2A); *Nostoc* PPC ssp.

Preferred embodiments of the invention thus do not include naturally occurring Mtd proteins, such as those with SEQ ID NO:20 (Mtd-P1 or *Bordetella* phage BPP-1) or variations thereof having the amino acid sequences of Mtd-P3c, Mtd-M1, Mtd-I1, or Mtd-U1. Naturally occurring selectins; MBPs; NKG2D; CD69; EMBP; TSG-6; and intimin as well as naturally occurring sequences of CTL-fold containing proteins from *Vibrio harveyi* ML phage (V.h. ML); *Bifidobacterium longum* (B.l.); *Bacteroides thetaiotaonicron* (B.t.); *Treponema denticola* (Td.); *Trichodesmium erythraeum* 1A (T.e. 1A); *Trichodesmium erythraeum* 1B (T.e. 1B); *Trichodesmium erythraeum* #2 (T.e. 2); *Nostoc* PPC ssp. 7120 #1 (N. PCC. 1); *Nostoc* PPC ssp. 7120 #2A (N. PCC. 2A); *Nostoc* PPC ssp. 7120 #2B (N. PCC. 2B); *Nostoc punctiforme* #1 (N.p. 1); and *Nostoc punctiforme* #2 (N.p. 2) having the corresponding sequences shown in FIG. 5 are also preferably not part of the present invention. These proteins are, however, disclosed as providing variable regions between the β3 and β5 strands of the CTL-fold contained therein for use in the presentation of a binding site as described herein. These proteins are also disclosed as providing CTL-folds for use with the binding sites and variable regions as described herein.

The invention also provides polynucleotides encoding the scaffolds and binding proteins described herein. The polynucleotides are preferably operably linked to a regulatory nucleic acid sequence that controls or regulates the expression of the coding polynucleotide in a cell or cell extract. A regulatory sequence refers to regions or sequence located upstream and/or downstream from the start of transcription that are involved in recognition and binding of RNA polymerase and other proteins to initiate transcription. The term includes a promoter for regulating start of transcription.

The polynucleotide may be part of a vector or plasmid used to propagate or amplify the polynucleotide. Where the polynucleotide is operably linked to a regulatory nucleic acid sequence, presence in a vector or plasmid permits the expression of the encoded scaffold or binding protein. This permits production and isolation of large quantities of a scaffold or binding protein of the invention.

Alternatively, the polynucleotide and regulatory sequence is operably linked to other sequences to form a diversity-generating retroelement (DGR) as described herein such that the variable residues of the binding site in the scaffold or binding protein may be readily diversified via a DGR. While embodiments of the invention based upon the nucleic acids encoding the sequences shown in FIG. 5 are readily used to diversify the binding sites contained therein, this aspect of the invention is advantageously applied to other CTL-folds and the binding sites contained therein where the region between the β3 and β5 strands are not a variable region until operably linked to a TR (and an IMH if necessary), as well as any other necessary components in cis or in trans, like reverse transcriptase activity as a non-limiting example, wherein the TR directs alterations of amino acid residues of the binding site, and thus variable region, as described herein. Of course this means to create alterations in the binding site is limited by adenine directed mutagenesis as described herein. But the invention also contemplates the use of traditional mutagenesis techniques for altering the binding specificity of the region between the β3 and β5 strands of a CTL-fold as described herein.

The polynucleotide, preferably as part of a DGR, may also be part of a phage or bacterial genome and expressed on the surface of phage or bacteria. DGR as used herein includes the use of mutagenic homing wherein an IMH directs mutagenesis of variable residues within the variable region (VR) of a scaffold or binding protein of the invention though a functionally linked TR, which directs alterations of nucleotide residues in the VR based on the locations of adenine residues at corresponding positions in the related TR sequence, as well as any other necessary components in cis or in trans, like reverse transcriptase activity as a non-limiting example. Use of a DGR advantageously permits use of the phage or bacteria to form a library expressing a heterogeneous population of encoded scaffolds or binding proteins on the surfaces of individual organisms. The use of "population" refers to a plurality of heterogeneous members which have similarities but at least two of which have different binding sites as described herein.

A population of diversified population of phage may be used in a method to identify a scaffold or binding protein as binding to a target molecule of interest. Non-limiting examples of such target molecules include a cell surface molecule, optionally of a cancer cell, an epithelial cell, an endothelial cell, and a bacterial or fungal cell surface molecule. In some embodiments of the invention, the scaffold or binding protein is expressed as part of the tail fiber in a bacteriophage particle.

Such a method may comprise expressing a population of scaffolds or binding proteins on the surfaces of members of a library of phage particles (including as part of the tail fiber(s), of bacteria or of other cells; contacting the members of the library with a target molecule of interest, optionally immobilized; removing members that do not bind to the target; and selecting the library member(s) that bind the target molecule of interest. Alternatively, the selected members can be propagated to form another library of members for an additional round of screening or selection using the above method. This permits the enrichment of library member(s) that bind the target of interest and also provides a means to verify the selected member(s) as binding the target. In some embodiments of the invention, the method further comprises isolating polynucleotides from the selected member(s). The phage library members are one form of a plurality, or family, of scaffolds or binding proteins of the invention.

A selected or identified scaffold or binding protein may also be "evolved" by a variation of the above to select for enhanced binding to the same ligand or binding to a different ligand. One method for evolving a previously identified or selected scaffold or binding protein is to provide a polynucleotide encoding the scaffold or binding protein, allow it to undergo diversification as described herein to produce a library of variants; and select for a member of the library with enhanced binding to the same target molecule or with "gain of function" binding to another target molecule.

Of course chemically or genetically known target molecules or unknown target molecules may be used to select or identify a scaffold or binding protein of the invention. Prior information regarding a target molecule's structure is not required to isolate a scaffold or binding protein that binds it. Preferably, the scaffold or binding protein will display specific binding affinity for a particular target, optionally with the functionality of blocking the binding of one or more other molecules to the target molecule. In the case of a cell surface ligand, the scaffold or binding protein may also be able to stimulate or inhibit a metabolic pathway, to act as a signal or messenger, or to stimulate or inhibit cellular activity. A scaffold or binding protein can thus be used as an antagonist, an agonist, as well as a modulator of a cell surface ligand function. A scaffold or binding protein for an "orphan" receptor to which no natural ligand is known may also be generated.

Unless otherwise defined herein, the use of "specifically binds" or "selectively binds" with respect to a scaffold or binding protein herein refers to binding interactions between the scaffold or binding protein and a first molecular entity that occurs to the exclusion of interactions with a second molecular entity present with the first in a heterogeneous population of molecules or other biological materials. Generally, a scaffold or binding protein of the invention binds to a target molecule better by at least about 2×, more preferably about 5× or about 10×, than binding to background molecules that are present or used as non-specific control targets.

The scaffolds and binding proteins of the invention may also be modified, such as by attachment of another moiety thereto. In some embodiments of the invention, the moiety may be a label, optionally a detectable label, including a directly detectable label such as a radioactive isotope, a fluorescent label (Cy3 and Cy5 as non-limiting examples) or a particulate label. Non-limiting examples of particulate labels include latex particles and colloidal gold particles. Alternatively, the label may be for indirect detection. Non-limiting examples include an enzyme, such as, but not limited to, luciferase, alkaline phosphatase, and horse radish peroxidase. Other non-limiting examples include a molecule bound by another molecule, such as, but not limited to, biotin, the Fc portion of an antibody, an affinity peptide, or a purification tag. Preferably, the label is covalently attached. The scaffold or binding protein may also be selected to bind antibodies from specific animals, e.g., goat, rabbit, mouse, etc., for use as a secondary reagent in assays using such antibodies as the primary detection agent.

Alternatively, a scaffold or binding protein of the invention may be detected directly by use of a reagent that binds thereto. Non-limiting examples include an antibody, or functional fragment thereof, that binds a portion of the scaffold without interference of the binding site or that binds a portion of the superscaffold without interfering with the binding site. Such an antibody or fragment thereof is preferably labeled for detection as described herein and as known in the art. Alternatively, a ligand for a portion of the scaffold or the superscaffold, which binds to a region distinct from, and without interference to, the binding site may be used. The ligand is also preferably labeled for detection as provided herein and known in the art.

Detection of a scaffold or binding protein of the invention may be advantageously used to detect the presence of a target molecule bound by the scaffold or binding protein. Such detection may also be used to detect the presence of a cell that expresses the ligand or molecule. Non-limiting detection assays in which the invention may be adapted include flow cytometry and fluorescent microscopy.

As an alternative non-limiting example, a labeled scaffold or binding protein of the invention which specifically binds human chorionic gonadotropin (hCG), to the exclusion of other factors that are normally found therewith, may be used to detect hCG in human urine samples as an indicator of pregnancy, such as by use of a lateral flow device as known in the art. Alternatively, a labeled scaffold or binding protein of the invention may be used to detect a microorganism, such as pathogenic bacteria or fungi by binding to a cell surface molecule specific to the microorganism of interest, relative to other organisms normally found therewith.

Thus the invention also provides a method of detecting a cell, the method comprising contacting a scaffold or binding protein of the invention which binds a cell surface molecule specific to the cell and subsequently detecting the bound scaffold or binding protein. Preferably, the cell is a bacterial or fungal cell, particularly pathogenic forms thereof. Alternatively, the cell may be associated with a disease or other unwanted condition, including, but not limited to a cancer cell or a virally infected cell.

Therefore, the invention provides for the use of a scaffold or binding protein as disclosed herein as a diagnostic agent, either in vitro or in vivo, based on its ability to bind to a tissue or disease associated target molecule. Tissue associated molecules are those that are expressed exclusively, or at a significantly higher level, in one or more tissue(s) compared to other tissues in an animal. Disease associated molecules are those that are expressed exclusively, or at a significantly higher level, in one or more diseased cells, diseased tissues, or bodily fluid in comparison to non-diseased cells, tissues, or fluids in an organism.

Non-limiting tissue or disease associated molecules are discussed in Tables I and II of U.S. Patent Publication No 2002/0107215. Non-limiting examples of tissues where target ligands bound by the scaffolds and binding proteins of the invention include liver, pancreas, adrenal gland, thyroid, salivary gland, pituitary gland, brain, spinal cord, lung, heart, breast, skeletal muscle, bone marrow, thymus, spleen, lymph node, colorectal, stomach, ovarian, small intestine, uterus, placenta, prostate, testis, colon, colon, gastric, bladder, trachea, kidney, and adipose tissue. Other non-limiting examples include tumor cells, tumor tissue sample, organ cells, blood cells, and cells of the skin, lung, heart, muscle, brain, mucosae, liver, intestine, spleen, stomach, lymphatic system, cervix, vagina, prostate, mouth, and tongue.

Non-limiting examples of diseases include, but are not limited to, an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathycandidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia; cancers including adenocarcinoma, leukemia, lymphoma, melanoma, myeloma, sarcoma, teratocarcinorna, and, in particular, a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and GerstmannStraussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. Exemplary disease or conditions include, e.g., MS, SLE, ITP, IDDM, MG, CLL, CD, RA, Factor VIII Hemophilia, transplantation, arteriosclerosis, Sjogren's Syndrome, Kawasaki Disease, AHA, ulcerative colitis, multiple myeloma, Glomerulonephritis, seasonal allergies, and IgA Nephropathy; and a cardiovascular disorder such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, complications of cardiac transplantation, arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery.

In other embodiments of the invention, a scaffold or binding protein is conjugated, optionally through a linker, to a toxin, pro-drug, or other molecule (e.g., a protein, nucleic acid, organic small molecule, etc.) suitable for use as a pharmaceutical or therapeutic agent. Non-limiting examples of proteins include cytokines, chemokines, growth factors, interleukins, cell-surface proteins, extracellular domains, cell surface receptors, and cytotoxins. The conjugated scaffold or binding protein delivers the attached molecule to a location bound by the binding site of the scaffold or binding protein. Such forms of the invention may be used in method of decreasing the viability of a cell, preferably a disease associated cell, such as a cancer cell or virally infected cell. Stated differently, the invention provides a method of targeting a cell expressing a cell surface molecule by use of a scaffold or binding protein of the invention. Such a method comprises contacting said cell with a scaffold or binding protein of the invention which binds said cell surface molecule.

In the case of a cancer cell, such as those of the cancers listed above, the scaffold or binding protein is one which preferably binds an external cell surface molecule of the cell with sufficient specificity to minimize undesirable binding to non-cancer cells. Similarly, in the case of a virally infected cell, the scaffold or binding protein is one which preferably binds a viral antigen expressed on the external cell surface of an infected cell with sufficient specificity to minimize undesirable binding to non-infected cells.

Thus the invention also provides a method of decreasing the viability of a cell, said method comprising covalently linking a cellular toxin or pro-drug to a scaffold or binding protein of the invention and contacting the linked scaffold or binding protein with a cell comprising a cell surface molecule bound by the scaffold or binding protein to decrease the viability of the cell. Preferably, the cell is a cancer cell, expressing a cell surface marker specific to the cancer cell as described above. Alternatively, the cell is a virally infected cell, expressing a viral antigen, on the cell surface, that is specific to virally infected cells as described above.

Alternatively, the invention provides for the selection of a scaffold or binding protein which binds a cell surface molecule such that the binding of one or multiple scaffolds or binding proteins to the cell through the molecule triggers, or is sufficient to activate, a cell death program in the bound cell. A non-limiting example of such a scaffold or binding protein is one that is analogous to Fas ligand or an antibody against Fas which triggers apoptosis of a cell upon binding to Fas expressed on the cell.

Therefore, the invention provides for the use of a scaffold or binding protein as disclosed herein as a therapeutic agent for use in the treatment of disease or other unwanted conditions. Alternatively, a scaffold or binding protein may be used in the prophylactic treatment of a disease or unwanted condition. The treatments of the invention include both in vivo or ex vivo administration. Preferably, the scaffold or binding protein is formulated as a composition comprising a pharmaceutically acceptable excipient, optionally for delayed release (or slow release over time). Sterile formulations of a scaffold or binding protein are also contemplated.

With respect to in vivo embodiments, a scaffold or binding protein is typically administered or transferred directly to the cells to be treated or to the tissue site of interest via intramuscular, intradermal, subdermal, subcutaneous, oral, intraperitoneal, intrathecal, or intravenous procedures. Alternatively, a scaffold or binding protein can be placed within a cavity of the body, such as during surgery, or by inhalation, or vaginal or rectal administration. With respect to ex vivo embodiments, the contacted cells are returned or delivered to the site from which they were obtained or to another site in the subject to be treated. The subject need not be that from which the cells were obtained. The treated cells may be optionally grafted onto a tissue or organ before being returned or alternatively delivered to the blood or lymph system using standard delivery or transfusion techniques.

Subjects that may be treated with a scaffold or binding protein of the invention include, but are not limited to, a mammal, including a human, primate, dog, cat, mouse, pig, cow, goat, rabbit, rat, guinea pig, hamster, horse, sheep; or a non-mammalian vertebrate such as a bird (e.g., a chicken or duck), or fish; or an invertebrate.

The invention also provides for compositions comprising a scaffold or binding protein disclosed herein. Non-limiting examples include attachment of a scaffold or binding protein to a surface, such as that of a tube, well, or dish; attachment to a matrix of an affinity material; or attachment to beads, a column, a solid support, or a microarray The compositions and methods of the present invention are ideally suited for preparation of kits produced in accordance with well known procedures. The invention thus provides kits comprising agents (like a scaffold or binding protein, or a library of scaffolds or binding proteins, described herein as non-limiting examples) for use in one or more methods as disclosed herein. Such kits, optionally comprising an agent with an identifying description or label or instructions relating to their use in the methods of the present invention, are provided. Such a kit may comprise containers, each with one or more of the various reagents (typically in concentrated form) or devices utilized in the methods. A set of instructions will also typically be included. Standards for calibrating the binding of a scaffold or binding protein to a ligand may also be included in the kits of the invention.

Alternatively a kit of the invention may comprise one or more reagents for production of a library of scaffolds or binding proteins, such as that embodied in phage particles which express individual members of the library. Such kits may contain vectors, such as initial phage particles, and cells for their propagation and plating as well as expression of scaffolds or binding proteins.

Having now generally described the invention, the same will be more readily understood through reference to the following examples which are provided by way of illustration, and are not intended to be limiting of the present invention, unless specified.

EXAMPLES

The following examples are offered to illustrate, but not to limit the claimed invention.

Example 1

Crystal Structures of Mtd Variants

Figure 3C:
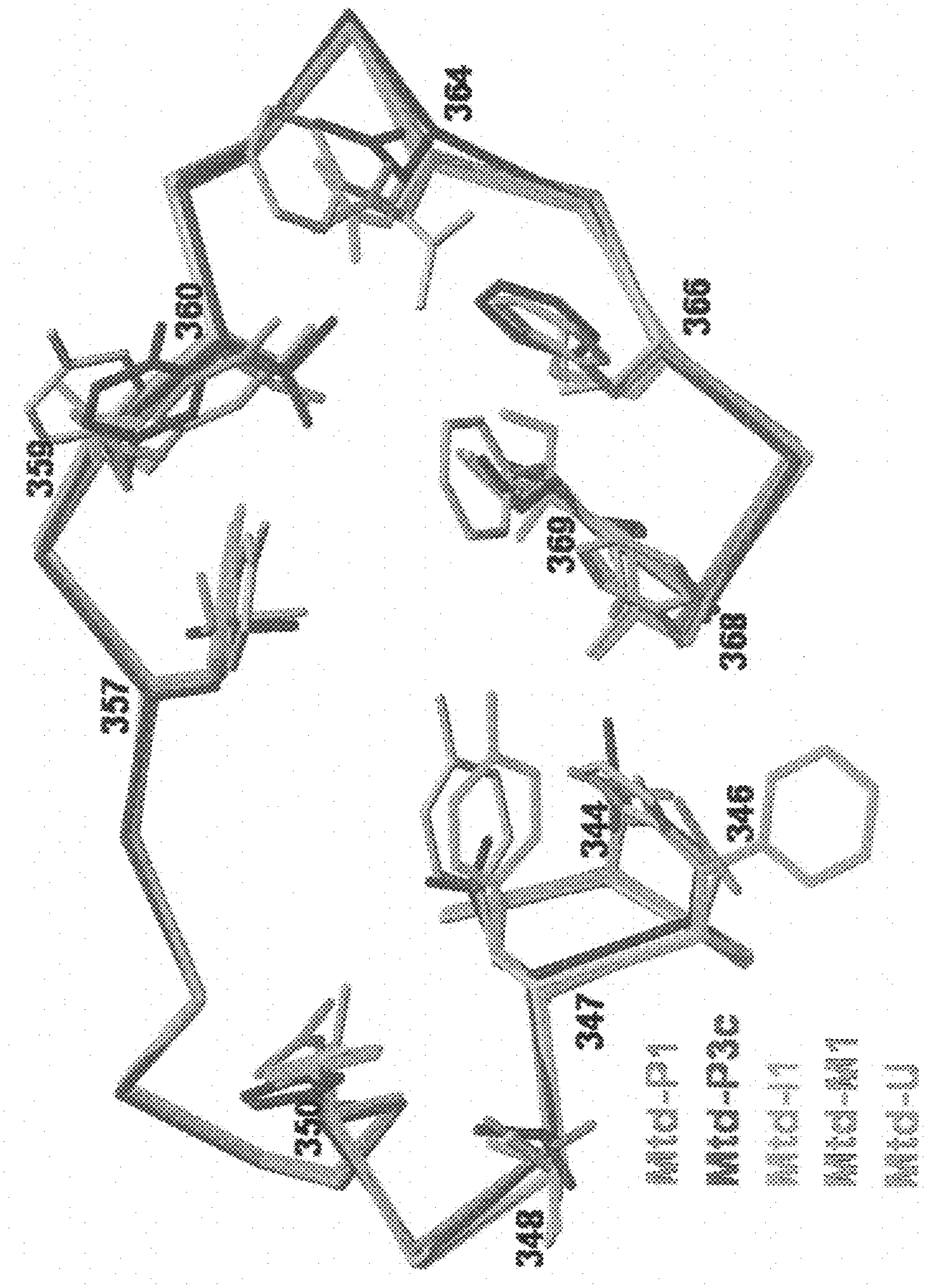
FIG. 3C shows a structural comparison of Mtd-P1, -3c, -M1, -I1, and -N1 used to determine that the main chain conformation of the CTL domain is remarkably consistent, despite half of the variable residues being on loop regions.

Structural comparison of Mtd-P1, -3c, -M1, -I1, and -N1 were used to discover that the main chain conformation of the CTL domain is remarkably invariant, despite half of the variable residues being on loop regions (FIG. 3C). The binding site in these variants is highly well ordered, having average main chain B-factors ranging from ~9 $Å^2$ in Mtd-P1 to ~24 $Å^2$ in Mtd-M1 and with density visible for all but one side chain (Phe-346 in Mtd-I1). Providing stabilization to these loops in Mtd are two features unique to the Mtd CTL-fold, namely the two inserts and trimeric assembly.

Figure 3D:
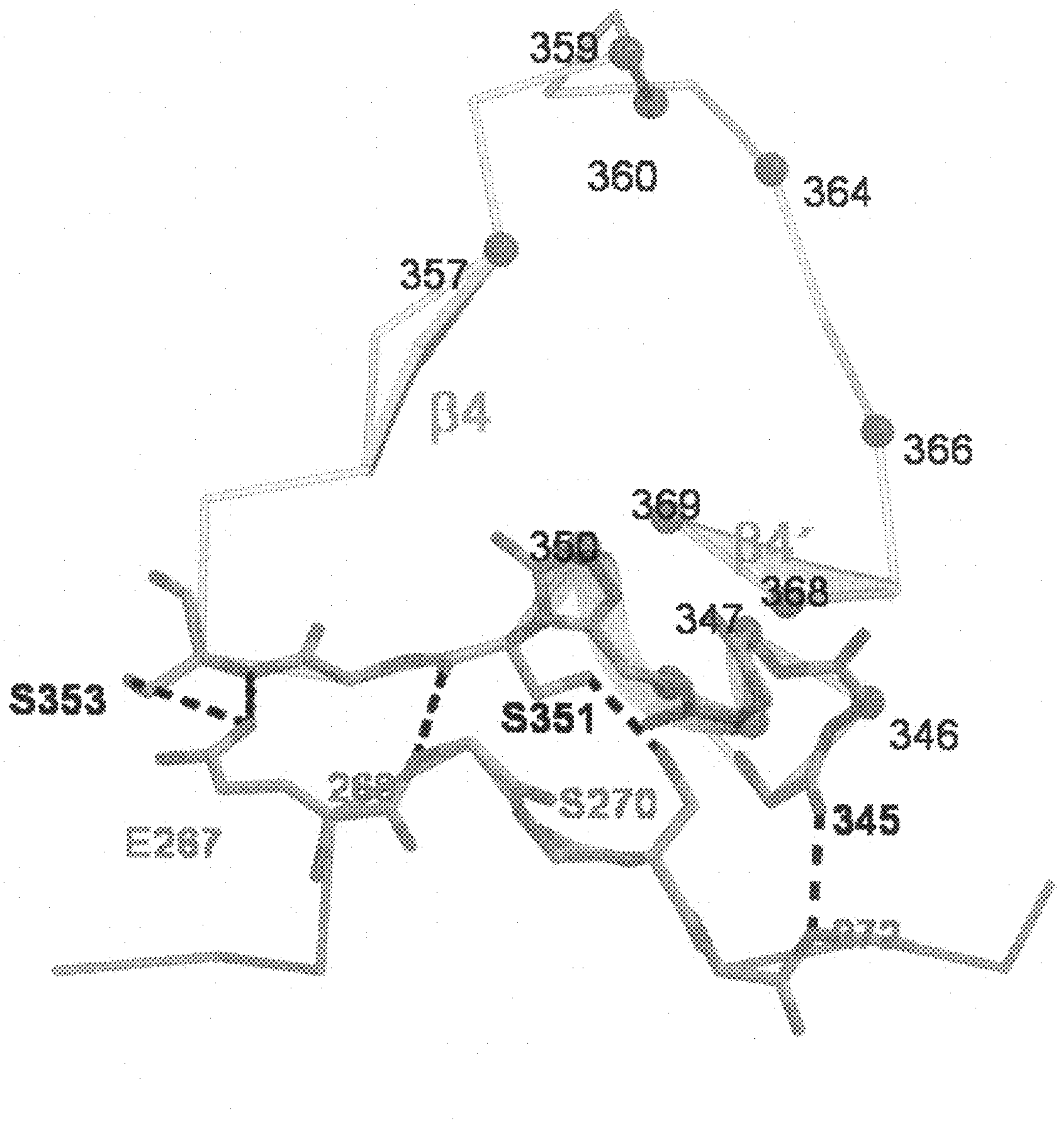
FIG. 3D shows a representation of Serine-270 (S270) and Glutamate-267 (E267) from the second insert in the Mtd CTL-fold forming hydrogen bonds to the invariant VR residues Serine-351 (S351) and Serine-353 (S353), respectively, within the binding region.
Figure 3E:
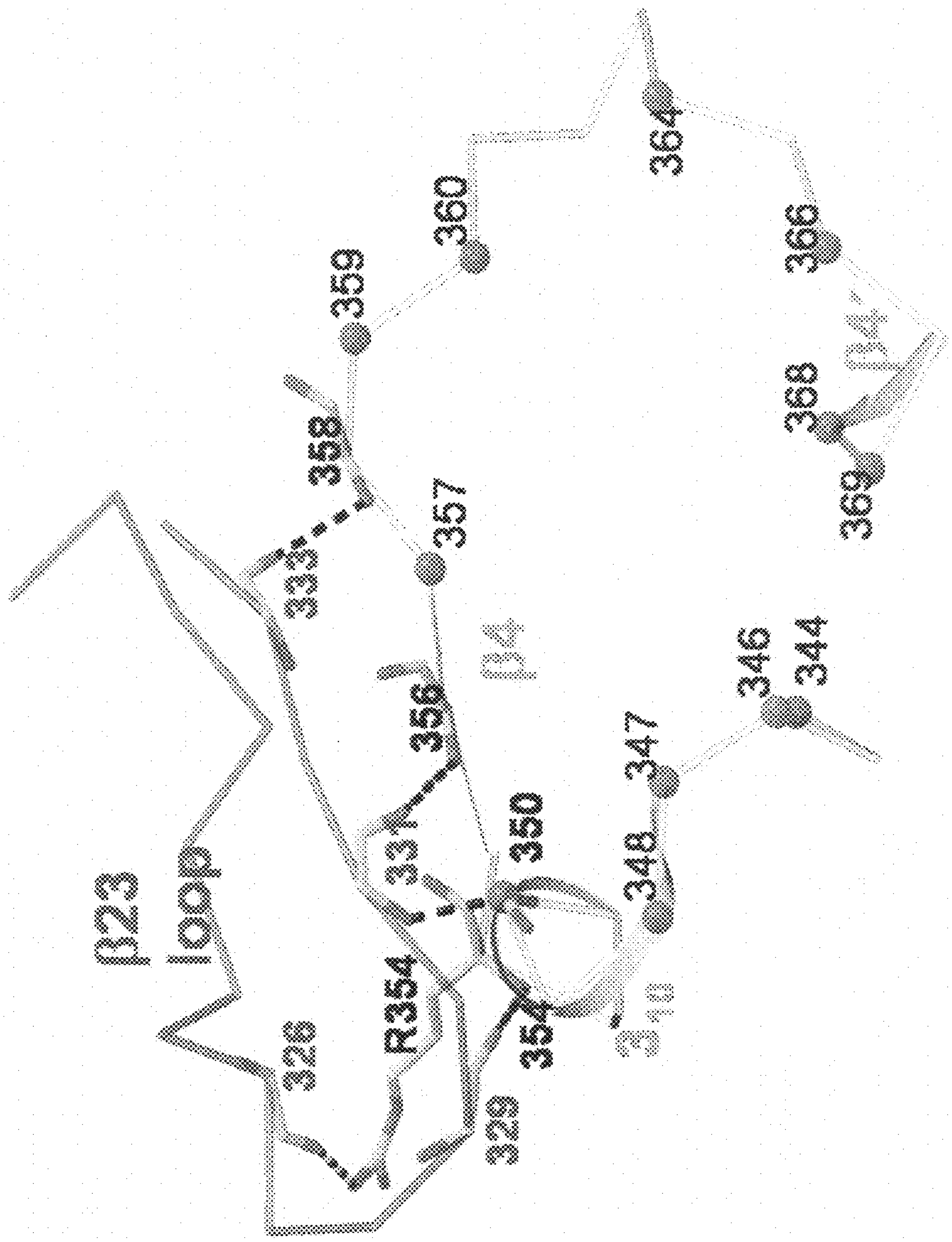
FIG. 3E shows that the β2β3 loop from one monomer hydrogen bonds to the invariant VR residue Arginine-354 (R354) and to main chain (scaffold) atoms of VR.

The inserts form hydrogen bonds to VR, including three to side chains of three invariant serines in VR. Ser-270 and Glu-267 from the second insert form hydrogen bonds to the invariant VR residues Ser-351 and Ser-353, respectively (FIG. 3D), and main chain atoms of the first insert form hydrogen bonds to invariant VR residue Ser-365 (not depicted). These interactions are supplemented by hydrogen bonds between the inserts and main chain (scaffold) atoms of the VR. Likewise, trimeric assembly contributes to stabilizing VR, specifically through contacts from a neighboring monomer's extensive β2β3 loop. The β2β3 loop from one monomer contributes not only the aforementioned invariant tyrosines (322 and 333) to a neighbor's binding site (FIG. 3B), but also hydrogen bonds to the invariant VR residue Arg-354 and to main chain (scaffold) atoms of VR (FIG. 3E). The β2β3 loop has the same intertwining conformation in all Mtd variants examined, being positioned over invariant residues (i.e., 351-356) in a neighbor's binding site.

Figure 1:
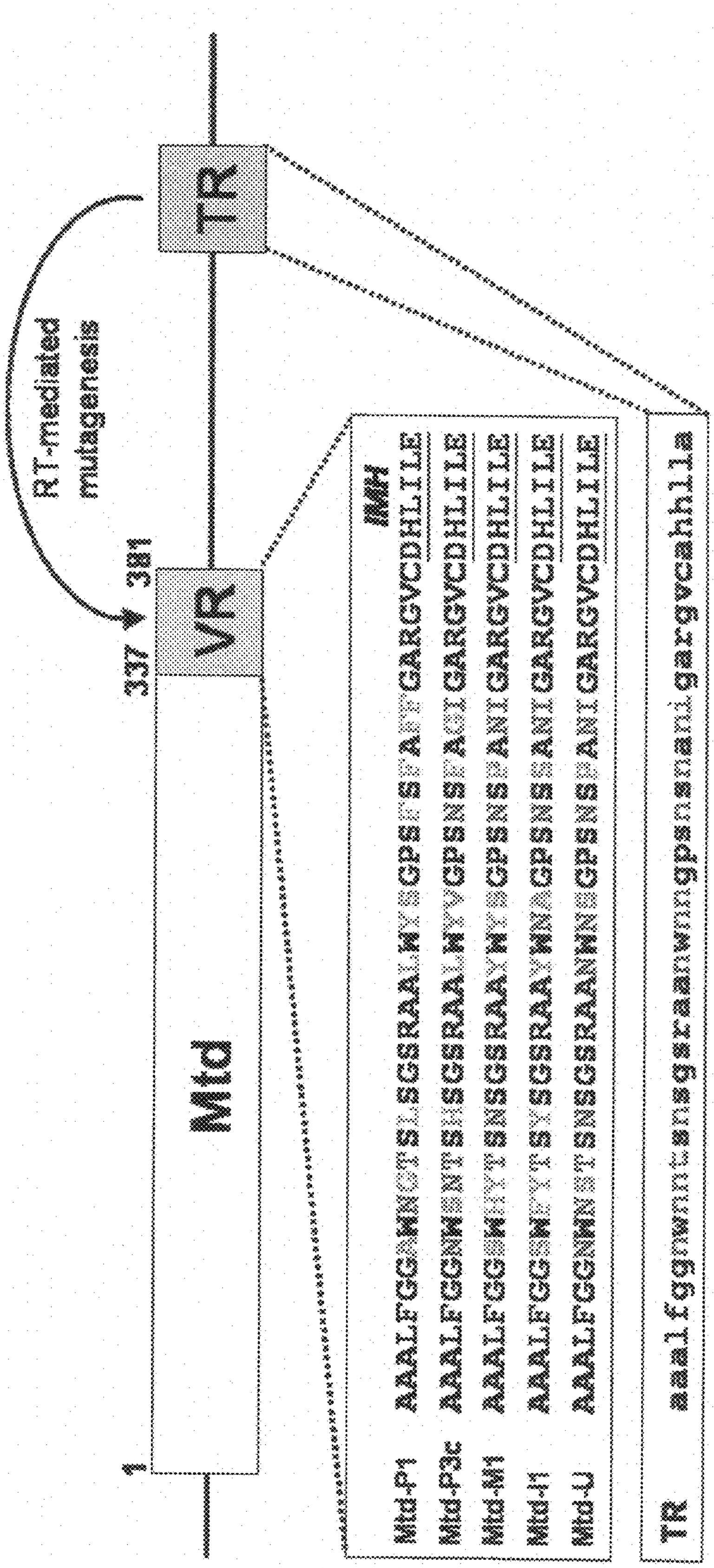
FIG. 1 shows the organization of the *Bordetella* phage DGR containing a single copy of Mtd with its VR followed by a nearly identical (90%), 134-bp direct repeat of the VR called the template repeat (TR), (SEQ ID NO:32) which is invariant among Mtd variants. The amino acid sequence of VR in each of the five Mtd variants (SEQ ID NOS:27-31)is shown in the upper box, together with the predicted amino acid sequence encoded by the corresponding nucleotide triplets of the TR in the lower box. The region corresponding to the initiation of mutagenic homing (IMH) sequence is underlined.
Figure 4:
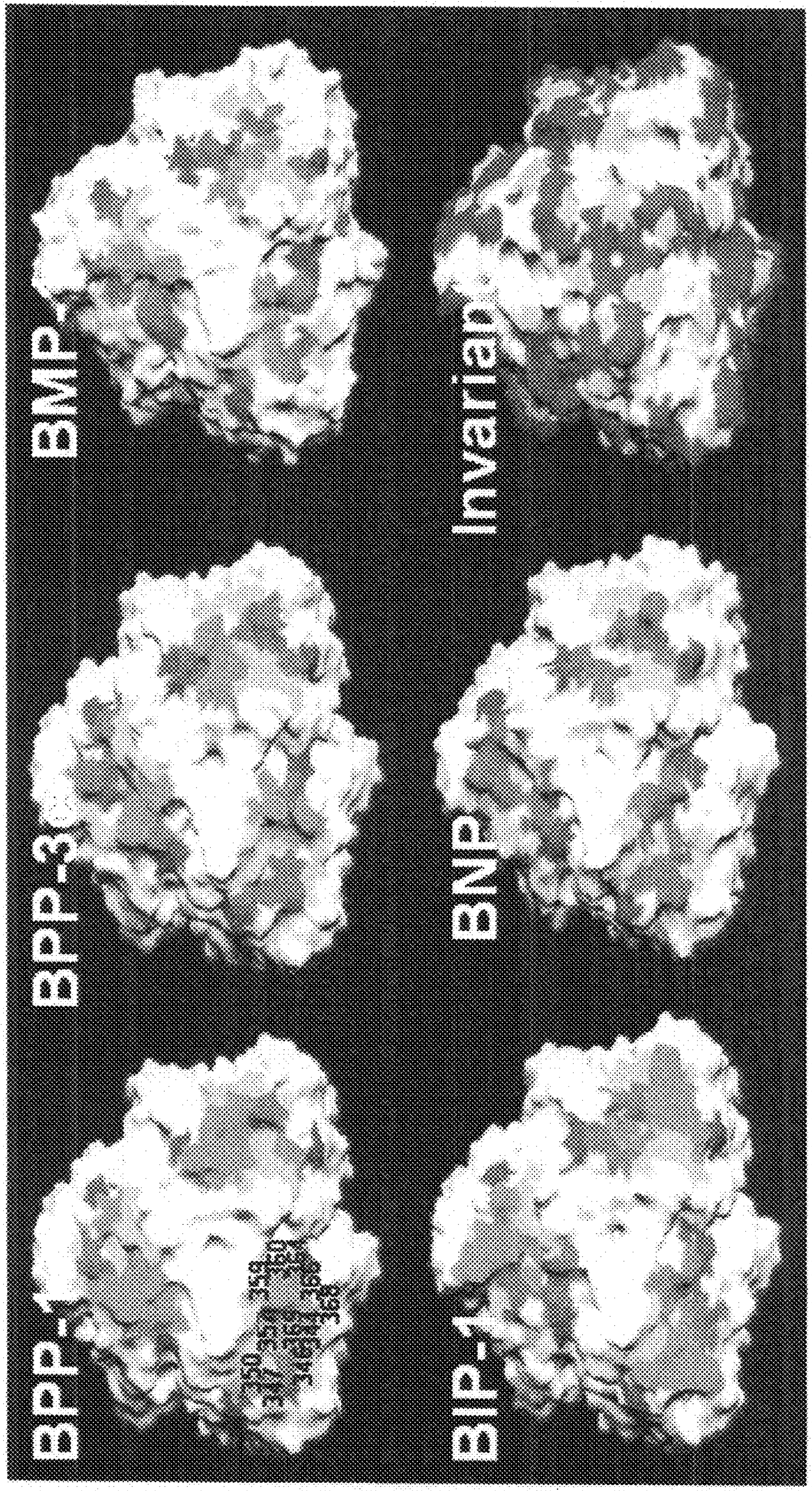
FIG. 4 shows by means of molecular surface representations that Mtd-P1 (BPP-1) and Mtd-I1 (BIP-1) have highly hydrophobic binding sites, and that the continuity of the hydrophobic surface decreases successively for Mtd-3c (BPP-3), -M1 (BMP-1), and -N1 (BNP). The view is looking onto the base of pyramid-shaped Mtd, that is, the surface that binds the exposed binding surface of the target molecule. The variable amino acid residues (except for 348) are numbered on the surface of BPP-1. The variable and invariant hydrophobic amino acid residues (Ala, Val, Leu, Ile, Phe, Tyr, Trp, and Met) are in green and yellow, respectively; and variable and invariant hydrophilic amino acid residues (Ser, Thr, Asn, Gln, Asp, Glu, His, Lys, Arg, and Cys) are in red and pink, respectively. The surface denoted 'Invariant' shows, using the same coloring scheme, the hydrophobic and hydrophilic surface surrounding the variable portion of the binding sites.

The binding sites of the five Mtd variants studied differ greatly in their pattern of hydrophobicities. FIG. 4A shows that Mtd-P1 and Mtd-I1 have highly hydrophobic binding sites, and that the continuity of the hydrophobic surface decreases successively for Mtd-3c, -M1, and -N1, with this last one having nine TR-encoded, mostly hydrophilic residues (FIG. 1). The binding sites of Mtd-P1 and -I1 accommodate four to five large, exposed hydrophobic residues, and although a preponderance of exposed hydrophobic surface is correlated with protein instability, both Mtd-P1 and -I1 are found to be highly stable proteins. The invariant area surrounding the binding site is largely hydrophilic, most likely aiding protein stability.

Example 2

Basis of Mtd to Ligand Interactions

To understand the basis of Mtd interactions with its ligand, a cell surface receptor, we characterized association between Mtd-P1 and the *Bordetella* receptor pertactin. The pertactin ectodomain (Prn-E) was incubated with Mtd variants and found by a coprecipitation assay to associate most strongly with Mtd-P1 but also with Mtd-3c and Mtd-M1. As a measure of specificity, Prn-E was not found to associate with Mtd-I1 or Mtd-N1. The three Mtd variants that are found to bind pertactin have in common the variable residue Tyr-359, previously shown by sequence comparison to be a consistent determinant for pertactin interaction. The presence of a tyrosine residue in the binding pocket is consistent with the presence of a number of hydrophobic surface-exposed patches on Prn-E (see Emsley, P., et al. Structure of *Bordetella pertussis* virulence factor P.69 pertactin. *Nature* 381, 90-2 (1996)). The maintenance of Prn affinity in some of these Mtd variants agrees with the relatively high frequency with which the phage adopts the BPP phenotype.

Despite each monomer providing a discrete binding site, the stoichiometry of association between Mtd and Prn-E is 3:1, as assessed by static light scattering. This may reflect steric occlusion of empty binding sites by elongated pertactin or pseudo-symmetric binding. The affinity of Mtd for Prn-E has a $K_D$ of ~3 μM as measured by isothermal titration calorimetry (ITC). Because *Bordetella* phage has six tail fibers with each fiber appearing to have two Mtd trimers, the affinity is likely translate to high avidity during infection. The ITC experiment also demonstrated that the endothermic interaction between the two molecules is entropically driven, as would be expected from the hydrophobic binding site of Mtd-P1. The affinity of Mtd-M1 for Prn-E is too low to be reliably measured by ITC, but a $K_D$ of ≧200 μM is estimated, suggesting that the boundary between a productive and non-productive interaction lies between 3 and ≧200 μM.

Example 3

CTL-Fold in Other DGRS

A number of other putative DGRs have been identified in phage and bacterial genomes. These resemble the *Bordetella* phage DGR in having sequence-related reverse transcriptases, similar arrangements of VR and TR, adenines constituting the main differences between VR and TR, and IMH-like elements at the end of VR. However, the putative variable proteins have no obvious sequence relationship to Mtd or other proteins. Because there appears to be no genetic requirement for VR and its IMH element to be positioned at the very C-terminus of a protein, the variations in positioning likely reflects the necessities of protein binding requirements as specified by the CTL-fold. Despite the low sequence identity among these proteins (~17%), we have been able to use the structure of Mtd along with considerations about variability to construct a sequence alignment consisting of the β2β3β4β4' sheet of the CTL-fold (see FIG. 5). Most notably, the invariant Mtd binding site residue Trp-345 is seen to be present in a highly conserved 'GGXW' motif. Invariant residues (Ser-351, Ser-353, Arg-354) involved in loop stabilization, trimeric contacts, or both are also generally conserved. As in Mtd, residues differing between VR and TR or ones that could potentially vary through an adenine-directed mechanism in these proteins are located chiefly between the β3 and β4' strands. These conclusions are bolstered by profile-based sequence alignment, which provides statistical confidence for the putative variable proteins from such diverse organisms as *Treponema denticola, Vibrio harveyi* ML phage, and the various cyanobacteria being related to Mtd and consequently having a CTL-fold.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A non-naturally occurring protein with a variable binding site, said protein comprising a C-type lectin fold (CTL-fold) wherein the variable binding site is located within the region between the β3 and β5 strands in the CTL-fold;

wherein the variable binding site is displayed and oriented by the CTL-fold;

and wherein the sequence variation within the variable binding site causes no conformational shifts in the CTL-fold greater than 1.8 Å.

2. The protein of claim 1 wherein said CTL-fold is a tropism determinant and wherein the protein is expressed on the exterior of a phage or bacterium.

3. The protein of claim 1 further comprising a label attached to said protein.

4. The protein of claim 3 wherein said label is a covalently attached, directly detectable label.

5. The protein of claim 1 further comprising a cellular toxin or pro-drug attached to said protein.

6. The protein of claim 1 wherein the variable binding site is selected from the group consisting of SEQ ID NOs: 1, 4, 5, 12, 14, 16, 18, 21, and 22.

7. The protein of claim 1 wherein the variable binding site is derived from a cyanobacterium, *Treponema denticola, Bifidobacterium longum, Bacteroides thetaiotaomicron*, or a *Vibrio harveji* ML phage protein.

8. The protein of claim 1 wherein the CTL-fold is bacterial or mammalian in origin.

9. The protein of claim 8 wherein the CTL-fold is a selectin, mannose binding protein, a natural killer receptor, an eosinophilic major basic protein, a tumour necrosis factor-stimulated gene product, an enteropathogenic *Eseherichia coli* intimin, or a *Yersinia pseudowberculosis* invasin.

* * * * *

SEQUENCE LISTING

```
<160> NUMBER OF SEQ ID NOS: 45

<210> SEQ ID NO 1
<211> LENGTH: 26
<212> TYPE: PRT
<213> ORGANISM: Artificial Sequence
<220> FEATURE:
<223> OTHER INFORMATION: Variable binding site of binding protein
      derived from Bordetella bacteriophage
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (3)..(5)
<223> OTHER INFORMATION: any
<220> FEATURE:
<221> NAME/KEY: MISC_FEATURE
<222> LOCATION: (7)..(7)
<223> OTHER INFORMATION: any
<220> FEATURE:
<221> NAME/KEY: MISC_FEATURE
<222> LOCATION: (14)..(14)
<223> OTHER INFORMATION: any
<220> FEATURE:
<221> NAME/KEY: MISC_FEATURE
<222> LOCATION: (16)..(17)
<223> OTHER INFORMATION: any
<220> FEATURE:
<221> NAME/KEY: MISC_FEATURE
<222> LOCATION: (21)..(21)
<223> OTHER INFORMATION: any
<220> FEATURE:
<221> NAME/KEY: MISC_FEATURE
<222> LOCATION: (23)..(23)
<223> OTHER INFORMATION: any
<220> FEATURE:
<221> NAME/KEY: MISC_FEATURE
<222> LOCATION: (25)..(26)
<223> OTHER INFORMATION: any

<400> SEQUENCE: 1

Xaa Trp Xaa Xaa Xaa Ser Xaa Ser Gly Ser Arg Ala Ala Xaa Trp Xaa
1               5                   10                  15

Xaa Gly Pro Ser Xaa Ser Xaa Ala Xaa Xaa
            20                  25


<210> SEQ ID NO 2
<211> LENGTH: 6
<212> TYPE: PRT
<213> ORGANISM: Artificial Sequence
<220> FEATURE:
<223> OTHER INFORMATION: Sequence extension at Xaa1 end derived from
      Bordetella bacteriophage

<400> SEQUENCE: 2

Ala Ala Leu Phe Gly Gly
1               5


<210> SEQ ID NO 3
<211> LENGTH: 12
<212> TYPE: PRT
<213> ORGANISM: Artificial Sequence
<220> FEATURE:
<223> OTHER INFORMATION: Sequence extension at Xaa12 end derived from
      Bordetella bacteriophage

<400> SEQUENCE: 3

Gly Ala Arg Gly Val Cys Asp His Leu Ile Leu Glu
```

-continued

```
1               5                   10


<210> SEQ ID NO 4
<211> LENGTH: 26
<212> TYPE: PRT
<213> ORGANISM: Artificial Sequence
<220> FEATURE:
<223> OTHER INFORMATION: Variable binding region of binding protein
      derived from Bordetella bacteriophage
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (3)..(7)
<223> OTHER INFORMATION: any
<220> FEATURE:
<221> NAME/KEY: MISC_FEATURE
<222> LOCATION: (9)..(10)
<223> OTHER INFORMATION: any
<220> FEATURE:
<221> NAME/KEY: MISC_FEATURE
<222> LOCATION: (12)..(26)
<223> OTHER INFORMATION: any

<400> SEQUENCE: 4

Xaa Trp Xaa Xaa Xaa Xaa Xaa Ser Xaa Xaa Arg Xaa Xaa Xaa Xaa Xaa
1               5                   10                  15

Xaa Xaa Xaa Xaa Xaa Xaa Xaa Xaa Xaa Xaa
            20                  25


<210> SEQ ID NO 5
<211> LENGTH: 26
<212> TYPE: PRT
<213> ORGANISM: Artificial Sequence
<220> FEATURE:
<223> OTHER INFORMATION: Cyanobacterium derived variable region
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (3)..(8)
<223> OTHER INFORMATION: any
<220> FEATURE:
<221> NAME/KEY: MISC_FEATURE
<222> LOCATION: (12)..(13)
<223> OTHER INFORMATION: any
<220> FEATURE:
<221> NAME/KEY: MISC_FEATURE
<222> LOCATION: (15)..(26)
<223> OTHER INFORMATION: any

<400> SEQUENCE: 5

Xaa Trp Xaa Xaa Xaa Xaa Xaa Xaa Cys Arg Ser Xaa Xaa Arg Xaa Xaa
1               5                   10                  15

Xaa Xaa Xaa Xaa Xaa Xaa Xaa Xaa Xaa Xaa
            20                  25


<210> SEQ ID NO 6
<211> LENGTH: 13
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 6

Gly Phe Arg Leu Val Ser Phe Pro Pro Arg Thr Leu Glu
```

-continued

```
1               5                   10


<210> SEQ ID NO 7
<211> LENGTH: 13
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 7

Gly Phe Arg Leu Val Ser Phe Pro Pro Arg Thr Pro Glu
1               5                   10


<210> SEQ ID NO 8
<211> LENGTH: 13
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 8

Gly Phe Arg Val Val Cys Ala Phe Gly Arg Ile Leu Gln
1               5                   10


<210> SEQ ID NO 9
<211> LENGTH: 13
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 9

Gly Phe Arg Val Val Cys Ala Phe Gly Arg Thr Phe Gln
1               5                   10


<210> SEQ ID NO 10
<211> LENGTH: 16
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 10

Gly Phe Arg Val Ile Ser Ser Ser Pro Val Val Ser Gly Phe His Ser
1               5                   10                  15


<210> SEQ ID NO 11
<211> LENGTH: 12
<212> TYPE: PRT
<213> ORGANISM: Artificial Sequence
<220> FEATURE:
<223> OTHER INFORMATION: Sequence extension at C terminus derived from
      cyanobacterium

<400> SEQUENCE: 11

Gly Cys Arg Val Val Val Val Arg Gly Arg Leu Ser
1               5                   10


<210> SEQ ID NO 12
<211> LENGTH: 33
<212> TYPE: PRT
<213> ORGANISM: Artificial Sequence
<220> FEATURE:
<223> OTHER INFORMATION: Treponema denticola derived variable region of
```

-continued binding protein
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (4)..(4)
<223> OTHER INFORMATION: any
<220> FEATURE:
<221> NAME/KEY: MISC_FEATURE
<222> LOCATION: (8)..(8)
<223> OTHER INFORMATION: any
<220> FEATURE:
<221> NAME/KEY: MISC_FEATURE
<222> LOCATION: (10)..(12)
<223> OTHER INFORMATION: any
<220> FEATURE:
<221> NAME/KEY: MISC_FEATURE
<222> LOCATION: (14)..(15)
<223> OTHER INFORMATION: any
<220> FEATURE:
<221> NAME/KEY: MISC_FEATURE
<222> LOCATION: (17)..(17)
<223> OTHER INFORMATION: any
<220> FEATURE:
<221> NAME/KEY: MISC_FEATURE
<222> LOCATION: (20)..(20)
<223> OTHER INFORMATION: any
<220> FEATURE:
<221> NAME/KEY: MISC_FEATURE
<222> LOCATION: (22)..(25)
<223> OTHER INFORMATION: any
<220> FEATURE:
<221> NAME/KEY: MISC_FEATURE
<222> LOCATION: (27)..(32)
<223> OTHER INFORMATION: any

<400> SEQUENCE: 12

Xaa Arg Val Xaa Arg Gly Gly Xaa Trp Xaa Xaa Xaa Ala Xaa Xaa Cys
1 5 10 15

Xaa Val Gly Xaa Arg Xaa Xaa Xaa Xaa Pro Xaa Xaa Xaa Xaa Xaa Xaa
20 25 30

Leu

<210> SEQ ID NO 13
<211> LENGTH: 8
<212> TYPE: PRT
<213> ORGANISM: Artificial Sequence
<220> FEATURE:
<223> OTHER INFORMATION: Sequence extension at C terminus derived from
T. denticola

<400> SEQUENCE: 13

Gly Phe Arg Leu Ala Cys Arg Pro
1 5

<210> SEQ ID NO 14
<211> LENGTH: 44
<212> TYPE: PRT
<213> ORGANISM: Artificial Sequence
<220> FEATURE:
<223> OTHER INFORMATION: Alternate phage-derived variable region of
binding protein
<220> FEATURE:
<221> NAME/KEY: MISC_FEATURE
<222> LOCATION: (19)..(19)
<223> OTHER INFORMATION: any
<220> FEATURE:
<221> NAME/KEY: MISC_FEATURE
<222> LOCATION: (21)..(22)
<223> OTHER INFORMATION: any
<220> FEATURE:

-continued

<221> NAME/KEY: MISC_FEATURE
<222> LOCATION: (25)..(25)
<223> OTHER INFORMATION: any
<220> FEATURE:
<221> NAME/KEY: MISC_FEATURE
<222> LOCATION: (32)..(32)
<223> OTHER INFORMATION: any
<220> FEATURE:
<221> NAME/KEY: MISC_FEATURE
<222> LOCATION: (34)..(35)
<223> OTHER INFORMATION: any
<220> FEATURE:
<221> NAME/KEY: MISC_FEATURE
<222> LOCATION: (39)..(39)
<223> OTHER INFORMATION: any
<220> FEATURE:
<221> NAME/KEY: MISC_FEATURE
<222> LOCATION: (41)..(44)
<223> OTHER INFORMATION: any

<400> SEQUENCE: 14

```
Gly Gly Gly Leu Trp Cys Arg Asn Tyr Gly Asp Arg Phe Pro Leu Arg
1               5                   10                  15

Gly Gly Xaa Trp Xaa Xaa Gly Ser Xaa Ala Gly Leu Gly Ala Leu Xaa
            20                  25                  30

Leu Xaa Xaa Ala Arg Ser Xaa Ser Xaa Xaa Xaa Xaa
        35                  40
```

<210> SEQ ID NO 15
<211> LENGTH: 8
<212> TYPE: PRT
<213> ORGANISM: Artificial Sequence
<220> FEATURE:
<223> OTHER INFORMATION: Sequence extension at Xaa12 end derived from alternate phage

<400> SEQUENCE: 15

```
Gly Phe Arg Pro Ala Phe Phe Val
1               5
```

<210> SEQ ID NO 16
<211> LENGTH: 30
<212> TYPE: PRT
<213> ORGANISM: Artificial Sequence
<220> FEATURE:
<223> OTHER INFORMATION: Bifidobacterium longum derived variable region of binding protein
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (5)..(5)
<223> OTHER INFORMATION: any
<220> FEATURE:
<221> NAME/KEY: MISC_FEATURE
<222> LOCATION: (7)..(8)
<223> OTHER INFORMATION: any
<220> FEATURE:
<221> NAME/KEY: MISC_FEATURE
<222> LOCATION: (18)..(18)
<223> OTHER INFORMATION: any
<220> FEATURE:
<221> NAME/KEY: MISC_FEATURE
<222> LOCATION: (20)..(22)
<223> OTHER INFORMATION: any
<220> FEATURE:
<221> NAME/KEY: MISC_FEATURE
<222> LOCATION: (25)..(25)
<223> OTHER INFORMATION: any
<220> FEATURE:
<221> NAME/KEY: MISC_FEATURE -continued

```
<222> LOCATION: (27)..(27)
<223> OTHER INFORMATION: any
<220> FEATURE:
<221> NAME/KEY: MISC_FEATURE
<222> LOCATION: (29)..(30)
<223> OTHER INFORMATION: any

<400> SEQUENCE: 16

Xaa Arg Phe Gly Xaa Leu Xaa Xaa Gly Ala Ala Cys Gly Ala Phe Ala
1               5                   10                  15

Val Xaa Leu Xaa Xaa Xaa Leu Ala Xaa Arg Xaa Trp Xaa Xaa
            20                  25                  30


<210> SEQ ID NO 17
<211> LENGTH: 12
<212> TYPE: PRT
<213> ORGANISM: Artificial Sequence
<220> FEATURE:
<223> OTHER INFORMATION: Sequence extension at Xaa12 end derived from
      B. longum

<400> SEQUENCE: 17

Gly Gly Arg Leu Ser Ala Leu Gly Arg Thr Lys Ala
1               5                   10


<210> SEQ ID NO 18
<211> LENGTH: 32
<212> TYPE: PRT
<213> ORGANISM: Artificial Sequence
<220> FEATURE:
<223> OTHER INFORMATION: Bacteroides thetaiotaonicron-derived variable
      region of binding protein
<220> FEATURE:
<221> NAME/KEY: MISC_FEATURE
<222> LOCATION: (3)..(3)
<223> OTHER INFORMATION: any
<220> FEATURE:
<221> NAME/KEY: MISC_FEATURE
<222> LOCATION: (10)..(14)
<223> OTHER INFORMATION: any
<220> FEATURE:
<221> NAME/KEY: MISC_FEATURE
<222> LOCATION: (16)..(17)
<223> OTHER INFORMATION: any
<220> FEATURE:
<221> NAME/KEY: MISC_FEATURE
<222> LOCATION: (19)..(19)
<223> OTHER INFORMATION: any
<220> FEATURE:
<221> NAME/KEY: MISC_FEATURE
<222> LOCATION: (21)..(21)
<223> OTHER INFORMATION: any
<220> FEATURE:
<221> NAME/KEY: MISC_FEATURE
<222> LOCATION: (24)..(24)
<223> OTHER INFORMATION: any
<220> FEATURE:
<221> NAME/KEY: MISC_FEATURE
<222> LOCATION: (26)..(26)
<223> OTHER INFORMATION: any
<220> FEATURE:
<221> NAME/KEY: MISC_FEATURE
<222> LOCATION: (29)..(32)
<223> OTHER INFORMATION: any

<400> SEQUENCE: 18

Tyr Gly Xaa Cys Trp Ser Ala Val Pro Xaa Xaa Xaa Xaa Xaa Gly Xaa
1               5                   10                  15

Xaa Leu Xaa Phe Xaa Ser Ser Xaa Val Xaa Pro Leu Xaa Xaa Xaa Xaa
            20                  25                  30
```

-continued

<210> SEQ ID NO 19
<211> LENGTH: 12
<212> TYPE: PRT
<213> ORGANISM: Artificial Sequence
<220> FEATURE:
<223> OTHER INFORMATION: Sequence extension at Xaa17 end derived from B. thetaiotaonicron

<400> SEQUENCE: 19

```
Arg Ala Cys Gly Phe Gly Leu Arg Ser Ser Gln Glu
1               5                   10
```

<210> SEQ ID NO 20
<211> LENGTH: 381
<212> TYPE: PRT
<213> ORGANISM: Bacteriophage protein

<400> SEQUENCE: 20

```
Met Ser Thr Ala Val Gln Phe Arg Gly Gly Thr Thr Ala Gln His Ala
1               5                   10                  15

Thr Phe Thr Gly Ala Ala Arg Glu Ile Thr Val Asp Thr Asp Lys Asn
            20                  25                  30

Thr Val Val Val His Asp Gly Ala Thr Ala Gly Gly Phe Pro Leu Ala
        35                  40                  45

Arg His Asp Leu Val Lys Thr Ala Phe Ile Lys Ala Asp Lys Ser Ala
    50                  55                  60

Val Ala Phe Thr Arg Thr Gly Asn Ala Thr Ala Ser Ile Lys Ala Gly
65                  70                  75                  80

Thr Ile Val Glu Val Asn Gly Lys Leu Val Gln Phe Thr Ala Asp Thr
                85                  90                  95

Ala Ile Thr Met Pro Ala Leu Thr Ala Gly Thr Asp Tyr Ala Ile Tyr
            100                 105                 110

Val Cys Asp Asp Gly Thr Val Arg Ala Asp Ser Asn Phe Ser Ala Pro
        115                 120                 125

Thr Gly Tyr Thr Ser Thr Thr Ala Arg Lys Val Gly Gly Phe His Tyr
    130                 135                 140

Ala Pro Gly Ser Asn Ala Ala Ala Gln Ala Gly Gly Asn Thr Thr Ala
145                 150                 155                 160

Gln Ile Asn Glu Tyr Ser Leu Trp Asp Ile Lys Phe Arg Pro Ala Ala
                165                 170                 175

Leu Asp Pro Arg Gly Met Thr Leu Val Ala Gly Ala Phe Trp Ala Asp
            180                 185                 190

Ile Tyr Leu Leu Gly Val Asn His Leu Thr Asp Gly Thr Ser Lys Tyr
        195                 200                 205

Asn Val Thr Ile Ala Asp Gly Ser Ala Ser Pro Lys Lys Ser Thr Lys
    210                 215                 220

Phe Gly Gly Asp Gly Ser Ala Ala Tyr Ser Asp Gly Ala Trp Tyr Asn
225                 230                 235                 240

Phe Ala Glu Val Met Thr His His Gly Lys Arg Leu Pro Asn Tyr Asn
                245                 250                 255

Glu Phe Gln Ala Leu Ala Phe Gly Thr Thr Glu Ala Thr Ser Ser Gly
            260                 265                 270

Gly Thr Asp Val Pro Thr Thr Gly Val Asn Gly Thr Gly Ala Thr Ser
        275                 280                 285

Ala Trp Asn Ile Phe Thr Ser Lys Trp Gly Val Val Gln Ala Ser Gly
    290                 295                 300

Cys Leu Trp Thr Trp Gly Asn Glu Phe Gly Gly Val Asn Gly Ala Ser
```

-continued

```
305                 310                 315                 320

Glu Tyr Thr Ala Asn Thr Gly Gly Arg Gly Ser Val Tyr Ala Gln Pro
                325                 330                 335

Ala Ala Ala Leu Phe Gly Gly Ala Trp Asn Gly Thr Ser Leu Ser Gly
            340                 345                 350

Ser Arg Ala Ala Leu Trp Tyr Ser Gly Pro Ser Phe Ser Phe Ala Phe
        355                 360                 365

Phe Gly Ala Arg Gly Val Cys Asp His Leu Ile Leu Glu
    370                 375                 380


<210> SEQ ID NO 21
<211> LENGTH: 13
<212> TYPE: PRT
<213> ORGANISM: Artificial Sequence
<220> FEATURE:
<223> OTHER INFORMATION: MBP derived variable region of binding protein
<220> FEATURE:
<221> NAME/KEY: MISC_FEATURE
<222> LOCATION: (1)..(2)
<223> OTHER INFORMATION: any
<220> FEATURE:
<221> NAME/KEY: MISC_FEATURE
<222> LOCATION: (4)..(4)
<223> OTHER INFORMATION: any
<220> FEATURE:
<221> NAME/KEY: MISC_FEATURE
<222> LOCATION: (8)..(9)
<223> OTHER INFORMATION: any
<220> FEATURE:
<221> NAME/KEY: MISC_FEATURE
<222> LOCATION: (11)..(13)
<223> OTHER INFORMATION: any

<400> SEQUENCE: 21

Xaa Xaa Gly Xaa Trp Asn Asp Xaa Xaa Cys Xaa Xaa Xaa
1               5                   10


<210> SEQ ID NO 22
<211> LENGTH: 18
<212> TYPE: PRT
<213> ORGANISM: Artificial Sequence
<220> FEATURE:
<223> OTHER INFORMATION: Selectin derived variable region of binding
      protein
<220> FEATURE:
<221> NAME/KEY: MISC_FEATURE
<222> LOCATION: (1)..(7)
<223> OTHER INFORMATION: any
<220> FEATURE:
<221> NAME/KEY: MISC_FEATURE
<222> LOCATION: (9)..(9)
<223> OTHER INFORMATION: any
<220> FEATURE:
<221> NAME/KEY: MISC_FEATURE
<222> LOCATION: (13)..(14)
<223> OTHER INFORMATION: any
<220> FEATURE:
<221> NAME/KEY: MISC_FEATURE
<222> LOCATION: (16)..(18)
<223> OTHER INFORMATION: any

<400> SEQUENCE: 22

Xaa Xaa Xaa Xaa Xaa Xaa Xaa Gly Xaa Trp Asn Asp Xaa Xaa Cys Xaa
1               5                   10                  15

Xaa Xaa


<210> SEQ ID NO 23
<211> LENGTH: 32
<212> TYPE: PRT
```

-continued

<213> ORGANISM: Artificial Sequence
<220> FEATURE:
<223> OTHER INFORMATION: Variable binding site of binding protein
      derived from Bordetella bacteriophage
<220> FEATURE:
<221> NAME/KEY: MISC_FEATURE
<222> LOCATION: (7)..(7)
<223> OTHER INFORMATION: any
<220> FEATURE:
<221> NAME/KEY: MISC_FEATURE
<222> LOCATION: (9)..(10)
<223> OTHER INFORMATION: any
<220> FEATURE:
<221> NAME/KEY: MISC_FEATURE
<222> LOCATION: (13)..(13)
<223> OTHER INFORMATION: any
<220> FEATURE:
<221> NAME/KEY: MISC_FEATURE
<222> LOCATION: (20)..(20)
<223> OTHER INFORMATION: any
<220> FEATURE:
<221> NAME/KEY: MISC_FEATURE
<222> LOCATION: (22)..(23)
<223> OTHER INFORMATION: any
<220> FEATURE:
<221> NAME/KEY: MISC_FEATURE
<222> LOCATION: (27)..(27)
<223> OTHER INFORMATION: any
<220> FEATURE:
<221> NAME/KEY: MISC_FEATURE
<222> LOCATION: (29)..(29)
<223> OTHER INFORMATION: any
<220> FEATURE:
<221> NAME/KEY: MISC_FEATURE
<222> LOCATION: (31)..(32)
<223> OTHER INFORMATION: any

<400> SEQUENCE: 23

Ala Ala Leu Phe Gly Gly Xaa Trp Xaa Xaa Thr Ser Xaa Ser Gly Ser
1               5                   10                  15

Arg Ala Ala Xaa Trp Xaa Xaa Gly Pro Ser Xaa Ser Xaa Ala Xaa Xaa
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Variable binding site of binding protein from
      Bordetella bacteriophage
<220> FEATURE:
<221> NAME/KEY: MISC_FEATURE
<222> LOCATION: (1)..(1)
<223> OTHER INFORMATION: any
<220> FEATURE:
<221> NAME/KEY: MISC_FEATURE
<222> LOCATION: (3)..(4)
<223> OTHER INFORMATION: any
<220> FEATURE:
<221> NAME/KEY: MISC_FEATURE
<222> LOCATION: (7)..(7)
<223> OTHER INFORMATION: any
<220> FEATURE:
<221> NAME/KEY: MISC_FEATURE
<222> LOCATION: (14)..(14)
<223> OTHER INFORMATION: any
<220> FEATURE:
<221> NAME/KEY: MISC_FEATURE
<222> LOCATION: (16)..(17)
<223> OTHER INFORMATION: any
<220> FEATURE:
<221> NAME/KEY: MISC_FEATURE
<222> LOCATION: (21)..(21)
<223> OTHER INFORMATION: any
<220> FEATURE:
<221> NAME/KEY: MISC_FEATURE -continued
<222> LOCATION: (23)..(23)
<223> OTHER INFORMATION: any
<220> FEATURE:
<221> NAME/KEY: MISC_FEATURE
<222> LOCATION: (25)..(26)
<223> OTHER INFORMATION: any

<400> SEQUENCE: 24

Xaa Trp Xaa Xaa Thr Ser Xaa Ser Gly Ser Arg Ala Ala Xaa Trp Xaa
1               5                   10                  15

Xaa Gly Pro Ser Xaa Ser Xaa Ala Xaa Xaa Gly Ala Arg Gly Val Cys
            20                  25                  30

<210> SEQ ID NO 25
<211> LENGTH: 38
<212> TYPE: PRT
<213> ORGANISM: Artificial Sequence
<220> FEATURE:
<223> OTHER INFORMATION: Variable binding site of binding protein from
      Bordetella bacteriophage
<220> FEATURE:
<221> NAME/KEY: MISC_FEATURE
<222> LOCATION: (7)..(7)
<223> OTHER INFORMATION: any
<220> FEATURE:
<221> NAME/KEY: MISC_FEATURE
<222> LOCATION: (9)..(10)
<223> OTHER INFORMATION: any
<220> FEATURE:
<221> NAME/KEY: MISC_FEATURE
<222> LOCATION: (13)..(13)
<223> OTHER INFORMATION: any
<220> FEATURE:
<221> NAME/KEY: MISC_FEATURE
<222> LOCATION: (20)..(20)
<223> OTHER INFORMATION: any
<220> FEATURE:
<221> NAME/KEY: MISC_FEATURE
<222> LOCATION: (22)..(23)
<223> OTHER INFORMATION: any
<220> FEATURE:
<221> NAME/KEY: MISC_FEATURE
<222> LOCATION: (27)..(27)
<223> OTHER INFORMATION: any
<220> FEATURE:
<221> NAME/KEY: MISC_FEATURE
<222> LOCATION: (29)..(29)
<223> OTHER INFORMATION: any
<220> FEATURE:
<221> NAME/KEY: MISC_FEATURE
<222> LOCATION: (31)..(32)
<223> OTHER INFORMATION: any

<400> SEQUENCE: 25

Ala Ala Leu Phe Gly Gly Xaa Trp Xaa Xaa Thr Ser Xaa Ser Gly Ser
1               5                   10                  15

Arg Ala Ala Xaa Trp Xaa Xaa Gly Pro Ser Xaa Ser Xaa Ala Xaa Xaa
            20                  25                  30

Gly Ala Arg Gly Val Cys
        35

<210> SEQ ID NO 26
<211> LENGTH: 38
<212> TYPE: PRT
<213> ORGANISM: Artificial Sequence
<220> FEATURE:
<223> OTHER INFORMATION: Variable binding site of binding protein from
      Bordetella bacteriophage
<220> FEATURE:
<221> NAME/KEY: MISC_FEATURE
<222> LOCATION: (1)..(1)
<223> OTHER INFORMATION: any -continued
<220> FEATURE:
<221> NAME/KEY: MISC_FEATURE
<222> LOCATION: (3)..(4)
<223> OTHER INFORMATION: any
<220> FEATURE:
<221> NAME/KEY: MISC_FEATURE
<222> LOCATION: (7)..(7)
<223> OTHER INFORMATION: any
<220> FEATURE:
<221> NAME/KEY: MISC_FEATURE
<222> LOCATION: (14)..(14)
<223> OTHER INFORMATION: any
<220> FEATURE:
<221> NAME/KEY: MISC_FEATURE
<222> LOCATION: (16)..(17)
<223> OTHER INFORMATION: any
<220> FEATURE:
<221> NAME/KEY: MISC_FEATURE
<222> LOCATION: (21)..(21)
<223> OTHER INFORMATION: any
<220> FEATURE:
<221> NAME/KEY: MISC_FEATURE
<222> LOCATION: (23)..(23)
<223> OTHER INFORMATION: any
<220> FEATURE:
<221> NAME/KEY: MISC_FEATURE
<222> LOCATION: (25)..(26)
<223> OTHER INFORMATION: any

<400> SEQUENCE: 26

```
Xaa Trp Xaa Xaa Thr Ser Xaa Ser Gly Ser Arg Ala Ala Xaa Trp Xaa
1               5                   10                  15

Xaa Gly Pro Ser Xaa Ser Xaa Ala Xaa Xaa Gly Ala Arg Gly Val Cys
            20                  25                  30

Asp His Leu Ile Leu Glu
        35
```

<210> SEQ ID NO 27
<211> LENGTH: 45
<212> TYPE: PRT
<213> ORGANISM: Artificial Sequence
<220> FEATURE:
<223> OTHER INFORMATION: Variable region of variant Mtd-P1

<400> SEQUENCE: 27

```
Ala Ala Ala Leu Phe Gly Gly Ala Trp Asn Gly Thr Ser Leu Ser Gly
1               5                   10                  15

Ser Arg Ala Ala Leu Trp Tyr Ser Gly Pro Ser Phe Ser Phe Ala Phe
            20                  25                  30

Phe Gly Ala Arg Gly Val Cys Asp His Leu Ile Leu Glu
        35                  40                  45
```

<210> SEQ ID NO 28
<211> LENGTH: 45
<212> TYPE: PRT
<213> ORGANISM: Artificial Sequence
<220> FEATURE:
<223> OTHER INFORMATION: Variable region of variant Mtd-P3c

<400> SEQUENCE: 28

```
Ala Ala Ala Leu Phe Gly Gly Asn Trp Ser Asn Thr Ser His Ser Gly
1               5                   10                  15

Ser Arg Ala Ala Leu Trp Tyr Val Gly Pro Ser Asn Ser Phe Ala Gly
            20                  25                  30

Ile Gly Ala Arg Gly Val Cys Asp His Leu Ile Leu Glu
        35                  40                  45
```

-continued

<210> SEQ ID NO 29
<211> LENGTH: 45
<212> TYPE: PRT
<213> ORGANISM: Artificial Sequence
<220> FEATURE:
<223> OTHER INFORMATION: Variable region of variant Mtd-M1

<400> SEQUENCE: 29

```
Ala Ala Ala Leu Phe Gly Gly Ser Trp His Tyr Thr Ser Asn Ser Gly
1               5                   10                  15

Ser Arg Ala Ala Tyr Trp Tyr Ser Gly Pro Ser Asn Ser Pro Ala Asn
            20                  25                  30

Ile Gly Ala Arg Gly Val Cys Asp His Leu Ile Leu Glu
        35                  40                  45
```

<210> SEQ ID NO 30
<211> LENGTH: 45
<212> TYPE: PRT
<213> ORGANISM: Artificial Sequence
<220> FEATURE:
<223> OTHER INFORMATION: Variable region of variant Mtd-11

<400> SEQUENCE: 30

```
Ala Ala Ala Leu Phe Gly Gly Ser Trp Phe Tyr Thr Ser Tyr Ser Gly
1               5                   10                  15

Ser Arg Ala Ala Tyr Trp Asn Ala Gly Pro Ser Asn Ser Ser Ala Asn
            20                  25                  30

Ile Gly Ala Arg Gly Val Cys Asp His Leu Ile Leu Glu
        35                  40                  45
```

<210> SEQ ID NO 31
<211> LENGTH: 45
<212> TYPE: PRT
<213> ORGANISM: Artificial Sequence
<220> FEATURE:
<223> OTHER INFORMATION: Variable region of variant Mtd-U

<400> SEQUENCE: 31

```
Ala Ala Ala Leu Phe Gly Gly Asn Trp Asn Ser Thr Ser Asn Ser Gly
1               5                   10                  15

Ser Arg Ala Ala Asn Trp Asn Ser Gly Pro Ser Asn Ser Pro Ala Asn
            20                  25                  30

Ile Gly Ala Arg Gly Val Cys Asp His Leu Ile Leu Glu
        35                  40                  45
```

<210> SEQ ID NO 32
<211> LENGTH: 45
<212> TYPE: PRT
<213> ORGANISM: Artificial Sequence
<220> FEATURE:
<223> OTHER INFORMATION: Template repeat of variable region of
      Bordetella phage DGR

<400> SEQUENCE: 32

```
Ala Ala Ala Leu Phe Gly Gly Asn Trp Asn Asn Thr Ser Asn Ser Gly
1               5                   10                  15

Ser Arg Ala Ala Asn Trp Asn Asn Gly Pro Ser Asn Ser Asn Ala Asn
            20                  25                  30

Ile Gly Ala Arg Gly Val Cys Ala His His Leu Leu Ala
        35                  40                  45
```

<210> SEQ ID NO 33
<211> LENGTH: 77

-continued

<212> TYPE: PRT
<213> ORGANISM: Artificial Sequence
<220> FEATURE:
<223> OTHER INFORMATION: Sequence of B2B3B4B4' sheet of CTL-fold in Mtd-P1

<400> SEQUENCE: 33

Cys Leu Trp Thr Trp Gly Asn Glu Phe Gly Gly Val Asn Gly Ala Ser
1 5 10 15

Glu Tyr Thr Ala Asn Thr Gly Gly Arg Gly Ser Val Tyr Ala Gln Pro
20 25 30

Ala Ala Ala Leu Phe Gly Gly Ala Trp Asn Gly Thr Ser Leu Ser Gly
35 40 45

Ser Arg Ala Ala Leu Trp Tyr Ser Gly Pro Ser Phe Ser Phe Ala Phe
50 55 60

Phe Gly Ala Arg Gly Val Cys Asp His Leu Ile Leu Glu
65 70 75

<210> SEQ ID NO 34
<211> LENGTH: 89
<212> TYPE: PRT
<213> ORGANISM: Artificial Sequence
<220> FEATURE:
<223> OTHER INFORMATION: Sequence of B2B3B4B4' sheet of CTL-fold in V. harveyi ML phage-derived protein of putative DGR

<400> SEQUENCE: 34

Tyr Pro Tyr Met His Asn Pro His Phe Ala Ala Ile Thr Lys Ser Ala
1 5 10 15

Gly Tyr Thr Pro Asn Glu Leu Leu Arg Arg Leu Leu Ile Glu Ser Ala
20 25 30

Thr Ala Thr Thr Val Gly Gly Gly Leu Trp Cys Arg Asn Tyr Gly Asp
35 40 45

Arg Phe Pro Ile Arg Gly Gly Tyr Trp Asn Asn Gly Ser Ser Ala Gly
50 55 60

Leu Gly Ala Leu Tyr Leu Ser Tyr Ala Arg Ser Asn Ser Asn Ser Ser
65 70 75 80

Ile Gly Phe Arg Pro Ala Phe Phe Val
85

<210> SEQ ID NO 35
<211> LENGTH: 86
<212> TYPE: PRT
<213> ORGANISM: Artificial Sequence
<220> FEATURE:
<223> OTHER INFORMATION: Sequence of B2B3B4B4' sheet of CTL-fold in B. longum-derived protein of putative DGR

<400> SEQUENCE: 35

Trp Arg Tyr Ala Glu Asp Phe Thr Leu Ser Asn Gly Val Leu Ile Pro
1 5 10 15

Thr Gly Ile Gly Ala Thr Ser Ala Thr Gly Leu Cys Asp Gly Val Tyr
20 25 30

Ala Asn Pro Leu Thr Ser Gln Gly Leu Arg Gln Val Arg Arg Phe Gly
35 40 45

Leu Leu Trp Asp Gly Ala Ala Cys Gly Ala Phe Ala Val Tyr Leu Ala
50 55 60

Asn Ala Leu Ala Asn Arg Trp Trp His Leu Gly Gly Arg Leu Ser Ala
65 70 75 80

Leu Gly Arg Thr Lys Ala

-continued

85

<210> SEQ ID NO 36
<211> LENGTH: 88
<212> TYPE: PRT
<213> ORGANISM: Artificial Sequence
<220> FEATURE:
<223> OTHER INFORMATION: Sequence of B2B3B4B4' sheet of CTL-fold in B. thetaiotaonicron-derived protein of putative DGR

<400> SEQUENCE: 36

Ile Asn Gly Thr Trp Asp Asp Ser Ser Lys Gly Trp Asn Phe Tyr Thr
1 5 10 15

Asp Pro Ser Lys Ser Lys Pro Asn Phe Phe Pro Ala Ser Gly Ser Arg
20 25 30

Asp Cys Ser Gly Gly Gly Ala Asn Ser Val Gly Phe Tyr Gly Val Cys
35 40 45

Trp Ser Ala Val Pro Tyr Ser Gln Tyr His Gly Cys Thr Leu Asp Phe
50 55 60

Ser Ser Ser Ser Val Tyr Pro Leu Leu Tyr Tyr Ser Arg Ala Cys Gly
65 70 75 80

Phe Gly Leu Arg Ser Ser Gln Glu
85

<210> SEQ ID NO 37
<211> LENGTH: 71
<212> TYPE: PRT
<213> ORGANISM: Artificial Sequence
<220> FEATURE:
<223> OTHER INFORMATION: Sequence of B2B3B4B4' sheet of CTL-fold in T. denticola-derived protein of putative DGR

<400> SEQUENCE: 37

Asn Val Ala Glu Trp Cys Trp Asp Trp Arg Ala Asp Ile His Thr Gly
1 5 10 15

Asp Ser Phe Pro Gln Asp Tyr Pro Gly Pro Ala Ser Gly Ser Gly Arg
20 25 30

Val Leu Arg Gly Gly Ser Trp Ala Gly Ser Ala Asp Tyr Cys Ala Val
35 40 45

Gly Glu Arg Val Asn Ile Ser Pro Gly Val Arg Cys Ser Asp Leu Gly
50 55 60

Phe Arg Leu Ala Cys Arg Pro
65 70

<210> SEQ ID NO 38
<211> LENGTH: 77
<212> TYPE: PRT
<213> ORGANISM: Artificial Sequence
<220> FEATURE:
<223> OTHER INFORMATION: Sequence of B2B3B4B4' sheet of CTL-fold in T. erythraeum 1A-derived protein of putative DGR

<400> SEQUENCE: 38

Cys Glu Asp Asp Met His Asp Asn Tyr Glu Gly Ala Pro Asn Asp Gly
1 5 10 15

Ser Pro Trp Leu Ser Gly Asn Gln Asn Thr Thr Lys Tyr Ser Thr Lys
20 25 30

Val Leu Arg Gly Gly Ser Trp Leu Asn Tyr Pro Trp Trp Cys Arg Ser
35 40 45

Ala Tyr Arg Tyr Asp Phe Ser Ser Asp Gly Ala Val Ile Ile Asn Phe
50 55 60

```
Gly Phe Arg Leu Val Ser Phe Pro Pro Arg Thr Leu Glu
65                  70                  75


<210> SEQ ID NO 39
<211> LENGTH: 77
<212> TYPE: PRT
<213> ORGANISM: Artificial Sequence
<220> FEATURE:
<223> OTHER INFORMATION: Sequence of B2B3B4B4' sheet of CTL-fold in
      T. erythraeum 1B-derived protein of putative DGR

<400> SEQUENCE: 39

Cys Glu Asp Asp Ser His Asp Asn Tyr Glu Gly Ala Pro Asn Asp Gly
1               5                   10                  15

Ser Pro Trp Val Ser Ser Asn Gln Asn Thr Thr Lys Tyr Thr Thr Lys
            20                  25                  30

Ile Leu Arg Gly Gly Ser Trp Tyr Asp Phe Pro Trp Trp Cys Arg Ser
        35                  40                  45

Ala Phe Arg Gly Tyr Tyr Phe Ser Val Glu Ala Val Asn Asp Phe Val
    50                  55                  60

Gly Phe Arg Leu Val Ser Phe Pro Pro Arg Thr Pro Glu
65                  70                  75


<210> SEQ ID NO 40
<211> LENGTH: 75
<212> TYPE: PRT
<213> ORGANISM: Artificial Sequence
<220> FEATURE:
<223> OTHER INFORMATION: Sequence of B2B3B4B4' sheet of CTL-fold in
      T. erythraeum #2-derived protein of putative DGR

<400> SEQUENCE: 40

Cys Leu Asp Thr Cys His Asp Asn Tyr Asn Gly Ala Pro Thr Asp Gly
1               5                   10                  15

Ser Ser Trp Glu Ser Gly Gly Asp Ser Asn Asp Arg Ile Leu Arg Gly
            20                  25                  30

Gly Cys Trp Ile His Asn Ser Phe Arg Cys Arg Ser Ala Trp Arg Asn
        35                  40                  45

Tyr Leu Tyr Ala Asp Tyr Leu Ser Asn Asp Arg Gly Phe Arg Val Ile
    50                  55                  60

Ser Ser Ser Pro Val Val Ser Gly Phe His Ser
65                  70                  75


<210> SEQ ID NO 41
<211> LENGTH: 71
<212> TYPE: PRT
<213> ORGANISM: Artificial Sequence
<220> FEATURE:
<223> OTHER INFORMATION: Sequence of B2B3B4B4' sheet of CTL-fold in
      Nostoc PPC #1-derived protein of putative DGR

<400> SEQUENCE: 41

Cys Gln Asp Glu Trp Gln Glu Asn Tyr Asn Asn Ala Pro Thr Asp Gly
1               5                   10                  15

Ser Ala Trp Leu Ile Asn Asn Asp Asn Gln Arg Arg Leu Leu Arg Gly
            20                  25                  30

Gly Ser Trp Asn Tyr Tyr Pro Arg Gly Cys Arg Ser Leu Ser Arg Leu
        35                  40                  45

Ser Asn Thr Arg Asp Asp Arg Asn Glu Arg Val Gly Cys Arg Val Val
    50                  55                  60
```

-continued

```
Val Val Arg Gly Arg Leu Ser
65                  70


<210> SEQ ID NO 42
<211> LENGTH: 80
<212> TYPE: PRT
<213> ORGANISM: Artificial Sequence
<220> FEATURE:
<223> OTHER INFORMATION: Sequence of B2B3B4B4' sheet of CTL-fold in
      Nostoc PPC #2A-derived protein of putative DGR

<400> SEQUENCE: 42

Cys Leu Asp Asp Trp His Asn Asn Tyr Lys Gly Ala Pro Thr Asp Gly
1               5                   10                  15

Ser Ala Trp Leu Asp Asn Asn Asp Asn Leu Tyr Gln Lys Gln Gly Ser
            20                  25                  30

Ala Val Leu Arg Gly Gly Ser Trp Asp Asp Leu Pro Glu Gly Cys Arg
        35                  40                  45

Ser Ala Ser Arg Leu Ser Leu Asn Arg Ala Val Arg Asp Leu Ile Leu
    50                  55                  60

Tyr Ser Phe Gly Phe Arg Val Val Cys Ala Phe Gly Arg Ile Leu Gln
65                  70                  75                  80


<210> SEQ ID NO 43
<211> LENGTH: 80
<212> TYPE: PRT
<213> ORGANISM: Artificial Sequence
<220> FEATURE:
<223> OTHER INFORMATION: Sequence of B2B3B4B4' sheet of CTL-fold in
      Nostoc PPC #2B-derived protein of putative DGR

<400> SEQUENCE: 43

Cys Leu Asp Asp Trp His Ser Ser Tyr Glu Gly Ala Pro Thr Asp Gly
1               5                   10                  15

Ser Ala Trp Phe Asp Asn Asn Asp Asn Leu Ser Gln Lys Gln Gly Gln
            20                  25                  30

Ala Val Leu Arg Gly Gly Ser Trp Ser Ser Ser Pro Val Val Cys Arg
        35                  40                  45

Ser Ala Ser Arg Gly Asn Asn Asp Arg Ala Gly Arg Val Tyr Arg Tyr
    50                  55                  60

Tyr Ala Val Gly Phe Arg Val Val Cys Ala Phe Gly Arg Thr Phe Gln
65                  70                  75                  80


<210> SEQ ID NO 44
<211> LENGTH: 80
<212> TYPE: PRT
<213> ORGANISM: Artificial Sequence
<220> FEATURE:
<223> OTHER INFORMATION: Sequence of B2B3B4B4' sheet of CTL-fold in
      N. punctiforme #1-derived protein of putative DGR

<400> SEQUENCE: 44

Cys Leu Asp Asp Trp His Asp Asn Tyr Glu Gly Ala Pro Thr Asp Gly
1               5                   10                  15

Ser Ala Trp Leu Asp Glu Asn Asp Asn Leu Tyr Gln Lys Gln Gly Arg
            20                  25                  30

Ala Val Leu Arg Gly Gly Ser Trp Phe Asn Asn Pro Asp Phe Cys Arg
        35                  40                  45

Ser Ala Ser Arg Val Ile Asn Ser Trp Ala Glu Arg Asp Asn Val Val
    50                  55                  60

Ser Asn Val Gly Phe Arg Val Val Cys Ala Phe Gly Arg Ile Leu Gln
```

-continued 65 70 75 80

<210> SEQ ID NO 45
<211> LENGTH: 80
<212> TYPE: PRT
<213> ORGANISM: Artificial Sequence
<220> FEATURE:
<223> OTHER INFORMATION: Sequence of B2B3B4B4' sheet of CTL-fold in N. punctiforme #2-derived protein of putative DGR

<400> SEQUENCE: 45

Cys Leu Asp Asp Trp His Asp Asn Tyr Glu Arg Ala Pro Thr Asp Gly
1 5 10 15

Ser Pro Trp Phe Asn Asp Asn Asp Ser Leu Tyr Gln Arg Gln Gly Asn
20 25 30

Ala Val Leu Arg Gly Gly Ser Trp Ile Phe Asp Pro Asp Tyr Cys Arg
35 40 45

Ser Ala Ser Arg Asn Leu Ser Tyr Arg Ala Glu Arg Asp Gly Ile Leu
50 55 60

Ser Thr Leu Gly Phe Arg Val Val Cys Ala Phe Gly Arg Ile Leu Gln
65 70 75 80